US012807622B2

(12) United States Patent
Xu et al.

(10) Patent No.: US 12,807,622 B2
(45) Date of Patent: Nov. 24, 2026

(54) CRYSTAL FORM OF PYRIMIDINE HETEROCYCLIC COMPOUND AND PREPARATION METHOD THEREFOR

(71) Applicant: D3 Bio (Wuxi) Co., Ltd., Wuxi JiangSu (CN)

(72) Inventors: Yangyang Xu, Shanghai (CN); Jikui Sun, Shanghai (CN); Wentao Wu, Shanghai (CN); Yang Zhang, Shanghai (CN); Shuhui Chen, Shanghai (CN)

(73) Assignee: D3 Bio (Wuxi) Co., Ltd., Wuxi (CN)

( * ) Notice: Subject to any disclaimer, the term of this patent is extended or adjusted under 35 U.S.C. 154(b) by 318 days.

(21) Appl. No.: 18/690,417

(22) PCT Filed: Sep. 9, 2022

(86) PCT No.: PCT/CN2022/118023

§ 371 (c)(1),
(2) Date: Mar. 8, 2024

(87) PCT Pub. No.: WO2023/036282

PCT Pub. Date: Mar. 16, 2023

(65) Prior Publication Data

US 2025/0129102 A1 Apr. 24, 2025

(30) Foreign Application Priority Data

Sep. 10, 2021 (CN) ......................... 202111062619.1
Aug. 26, 2022 (CN) ......................... 202211034826.0

(51) Int. Cl.
*C07D 519/00* (2006.01)
*A61K 31/519* (2006.01)
*A61P 35/00* (2006.01)

(52) U.S. Cl.
CPC .......... *C07D 519/00* (2013.01); *A61K 31/519* (2013.01); *A61P 35/00* (2018.01)

(58) Field of Classification Search
CPC ...... C07D 519/00; A61P 35/00; A61K 31/519
See application file for complete search history.

(56) References Cited

U.S. PATENT DOCUMENTS

| | | | |
|---|---|---|---|
| 10,590,115 B2 | 3/2020 | Planken et al. |
| 11,267,812 B2 | 3/2022 | Fischer et al. |
| 12,012,404 B2 | 6/2024 | Zhang et al. |
| 12,162,880 B2 | 12/2024 | Zhang et al. |
| 2019/0144444 A1 | 5/2019 | Blake et al. |
| 2022/0315598 A1 | 10/2022 | Xu et al. |
| 2023/0023009 A1 | 1/2023 | Kankanala et al. |
| 2023/0151004 A1 | 5/2023 | Zhang et al. |

FOREIGN PATENT DOCUMENTS

| | | | |
|---|---|---|---|
| CN | 112119075 A | 12/2020 |
| CN | 112390788 A | 2/2021 |
| CN | 112979664 A | 6/2021 |
| WO | 2020/239123 A1 | 12/2020 |
| WO | 2021/037018 A1 | 3/2021 |
| WO | WO-2021180181 A1 | 9/2021 |
| WO | WO-2022081655 A1 | 4/2022 |
| WO | WO-2023036282 A1 | 3/2023 |

OTHER PUBLICATIONS

Gura, Science Nov. 7, 1997: vol. 278. No. 5340, pp. 1041-1042.*
Cancer Drug Design and Discovery; Neidle, Stephen, ed. (Elsevier/Academic Press, 2008), Chapter 18.*
Co-pending U.S. Appl. No. 18/473,147, inventors Yang Zhang; et al., filed Sep. 22, 2023.
Patani et al., "Bioisosterism: A Rational Approach in Drug Design", Chem Rev, (Dec. 19, 1996), 96(8): 3147-3176. doi: 10.1021/cr950066q.
Roberts et al., "Trends in the Risks and Benefits to Patients with Cancer Participating in Phase 1 Clinical Trials", JAMA, (Nov. 3, 2004), 292(17): 2130-2140. doi: 10.1001/jama.292.17.2130.

* cited by examiner

*Primary Examiner* — Alicia L Otton
(74) *Attorney, Agent, or Firm* — Fenwick & West. LLP; Chen Chen; Rei Li

(57) ABSTRACT

A crystal form of a pyrimidine heterocyclic compound and a preparation method therefor. Specifically disclosed are a preparation method for and application of a compound of formula (II) and the crystal form thereof.

(II)

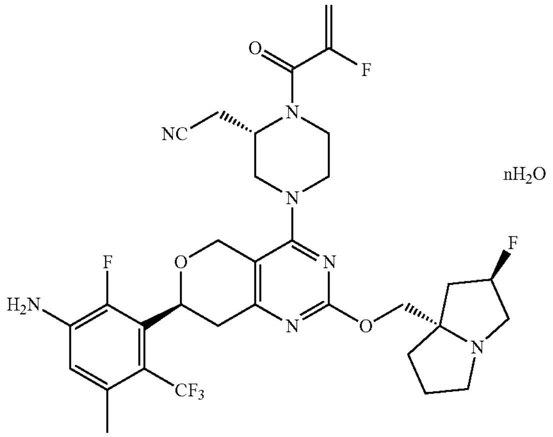

12 Claims, 3 Drawing Sheets

CRYSTAL FORM OF PYRIMIDINE HETEROCYCLIC COMPOUND AND PREPARATION METHOD THEREFOR

CROSS-REFERENCE TO RELATED APPLICATIONS

This application is a U.S. National Phase Application, filed under 35 U.S.C. § 371, of International Application No. PCT/CN2022/118023, filed on Sep. 9, 2022, which claims the priority to, and the benefit of, Chinese Application No. CN202111062619.1, filed on Sep. 10, 2021; and Chinese Application No. CN202211034826.0, filed on Aug. 26, 2022; the contents of each of which are incorporated herein by reference in their entireties.

TECHNICAL FIELD

The present disclosure relates to a crystal form of a class of pyrimidoheterocyclic compounds and a preparation method thereof, specifically to a preparation method and use of a compound represented by formula (II) and a crystal form thereof.

BACKGROUND

RAS oncogene mutations are the most common activating mutations in human cancers, occurring in 30% of human tumors. The RAS gene family includes three subtypes (KRAS, HRAS and NRAS), of which 85% of RAS-driven cancers are caused by mutations in the KRAS subtype. KRAS mutations are commonly found in solid tumors, such as lung adenocarcinoma, pancreatic ductal carcinoma and colorectal cancer, etc. In KRAS mutated tumors, 80% of oncogenic mutations occur at codon 12, and the most common mutations include: p.G12D (41%), p.G12V (28%) and p.G12C (14%).

The full name of KRAS gene is Kirsten rat sarcoma viraloncogene homolog. KRAS plays a pivotal role in the signaling regulation of cell growth. The upstream cell surface receptors such as EGFR (ErbB1), HER2 (ErbB2), ErbB3, and ErbB4, after receiving external signals, will transmit the signal to downstream through the RAS protein. When the KRAS protein is not activated, it binds tightly to GDP (guanosine diphosphate). After being activated by guanosine exchange factor such as SOS1, the KRAS protein binds to GTP (guanosine triphosphate) and becomes a kinase active state. After gene mutation, KRAS can independently transmit signals for growth and proliferation to downstream pathways independent of upstream growth factor receptor signals, causing uncontrolled cell growth and tumor progression. Meanwhile, whether KRAS gene has mutations or not is also an important indicator of tumor prognosis.

Although KRAS is the first oncogene to be discovered, it has long been considered an undruggable target. Until 2019, Amgen and Mirati Therapeutics successively published the clinical research results of their small molecule KRAS inhibitors AMG510 and MRTX849, which confirmed the clinical effectiveness of KRAS inhibitors in the clinical treatment of tumors for the first time. Both AMG 510 and MRTX849 are irreversible small molecule inhibitors that inhibit KRAS activity by forming irreversible covalent bonds with cysteine residues of KRAS G12C mutant protein.

KRAS plays a pivotal role in the signaling regulation of cell growth. The upstream cell surface receptors such as EGFR (ErbB1), HER2 (ErbB2), ErbB3, and ErbB4, after receiving external signals, will transmit the signal to downstream through the RAS protein. When the KRAS protein is not activated, it binds tightly to GDP (guanosine diphosphate). After being activated by guanosine exchange factor such as SOS1, the KRAS protein binds to GTP (guanosine triphosphate) and becomes a kinase active state. KRAS is an important member of RAS proteins. After gene mutation, KRAS can independently transmit signals for growth and proliferation to downstream pathways independent of upstream growth factor receptor signals, causing uncontrolled cell growth and tumor progression. Meanwhile, whether KRAS gene has mutations or not is also an important indicator of tumor prognosis.

Statistical results show that 12-36% of lung adenocarcinoma is driven by KRAS mutations: 27-56% of colon cancer is driven by KRAS; and 90% of pancreatic cancer, 21% of endometrial cancer, and 12-36% of lung adenocarcinoma are driven by KRAS, which indicate that the patient population is huge. In KRAS gene mutations, 97% of the mutations occur in amino acid residues at position 12 or 13, wherein G12D, G12V and G13D mutations have poor druggability, and KRAS (G12C) mutation in which glycine at position 12 is replaced by cysteine provides a good direction for the development of covalent inhibitors.

SUMMARY

The present disclosure provides a compound of formula (II), (II)

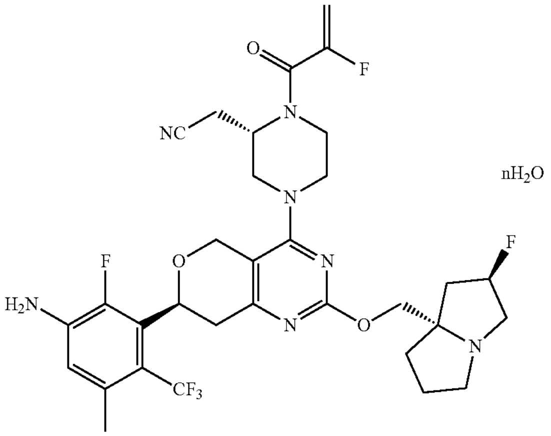

wherein n is selected from 0 to 3.

In some embodiments of the present disclosure, the n is selected from 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, and 3.0.

In some embodiments of the present disclosure, the n is selected from 0.5, 1, 1.5, 2, 2.5, and 3.

In some embodiments of the present disclosure, the n is 2.

The present disclosure also provides a compound of formula (II), (II)

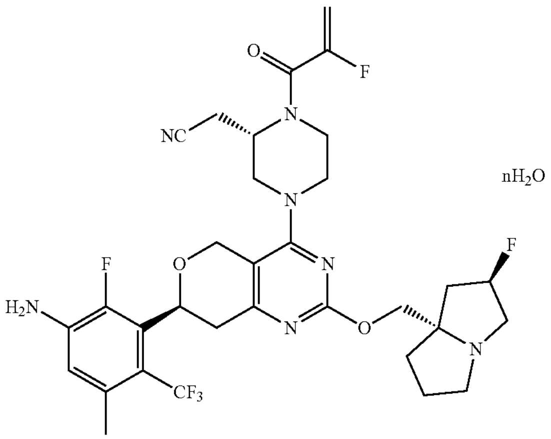

wherein n is selected from 0 to 2.

In some embodiments of the present disclosure, the n is selected from 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, and 2.

In some embodiments of the present disclosure, the n is selected from 0.5, 1, 1.5, and 2.

In some embodiments of the present disclosure, the n is 2.

The present disclosure also provides a crystal form A of the compound of formula (II), which is characterized by X-ray powder diffraction pattern with characteristic diffraction peaks at 2θ angles of 8.514±0.200°, 14.689±0.200°, and 18.122±0.200°.

In some embodiments of the present disclosure, the above crystal form A has X-ray powder diffraction pattern with characteristic diffraction peaks at 2θ angles of 6.218±0.200°, 8.514±0.200°, 12.299±0.200°, 14.689±0.200°, 16.903±0.200°, 18.122±0.200°, 18.927±0.200°, and 25.580±0.200°.

In some embodiments of the present disclosure, the above crystal form A has X-ray powder diffraction pattern with characteristic diffraction peaks at 2θ angles of 6.218±0.200°, 8.514±0.200°, 11.663±0.200°, 12.299±0.200°, 14.689±0.200°, 16.903±0.200°, 18.122±0.200°, 18.927±0.200°, 19.364±0.200°, 20.3860.200°, 21.914±0.200°, and 25.580±0.200°.

In some embodiments of the present disclosure, the above crystal form A has X-ray powder diffraction pattern with characteristic diffraction peaks at 2θ angles of 6.218±0.200°, 8.514±0.200°, 11.663±0.200°, 12.299±0.200°, 14.689±0.200°, 16.903±0.200°, 18.122±0.200°, 18.927±0.200°, 19.364±0.200°, 20.386±0.200°, 21.914±0.200°, 22.640±0.200°, 25.580±0.200°, 25.9880.200°, 27.147±0.200°, and 27.7150.200°.

In some embodiments of the present disclosure, the above crystal form A has X-ray powder diffraction pattern with characteristic diffraction peaks at 2θ angles of 6.218°, 8.514°, 11.663°, 12.299°, 14.689°, 16.903°, 18.122°, 18.554°, 18.927°, 19.364°, 20.386°, 21.914°, 22.640°, 23.867°, 24.553°, 24.806°, 25.580°, 25.988°, 27.147°, 27.715°, 29.135°, and 31.799°.

In some embodiments of the present disclosure, the above crystal form A has X-ray powder diffraction pattern with characteristic diffraction peaks at 2θ angles of 8.514±0.200° and 14.689±0.200°, and also optionally at 2θ angles of 6.218±0.200°, and/or 11.663±0.200°, and/or 12.299±0.200°, and/or 16.903±0.200°, and/or 18.122±0.200°, and/or 18.554±0.200°, and/or 18.927±0.200°, and/or 19.364±0.200°, and/or 20.386±0.200°, and/or 21.914±0.200°, and/or 22.64±0.200°, and/or 23.867±0.200°, and/or 24.5530.200°, and/or 24.806±0.200°, and/or 25.58±0.200°, and/or 25.988±0.200°, and/or 27.147±0.200°, and/or 27.715±0.200°, and/or 29.135±0.200°, and/or 31.799±0.200°.

In some embodiments of the present disclosure, disclosed is the above crystal form A, which has an XRPD pattern as shown in FIG. 1.

In some embodiments of the present disclosure, the XRPD pattern resolution data of the above crystal form A is shown in Table 1:

TABLE 1

| No. | 2θ Angle (°) | D-spacing (Å) | Relative intensity (%) | Intensity |
|---|---|---|---|---|
| 1 | 6.218 | 14.20235 | 49.70% | 1417.41 |
| 2 | 8.514 | 10.37753 | 53.00% | 1500.55 |
| 3 | 11.663 | 7.58177 | 27.40% | 865.097 |
| 4 | 12.299 | 7.19077 | 36.40% | 1111.73 |
| 5 | 12.888 | 6.86372 | 3.20% | 251.582 |
| 6 | 14.689 | 6.02570 | 100.00% | 2804.39 |
| 7 | 16.255 | 5.44860 | 2.80% | 288.118 |
| 8 | 16.903 | 5.24119 | 48.50% | 1486.90 |
| 9 | 18.122 | 4.89132 | 73.90% | 2150.25 |
| 10 | 18.554 | 4.77818 | 23.10% | 823.078 |
| 11 | 18.927 | 4.68486 | 44.30% | 1370.18 |
| 12 | 19.364 | 4.58024 | 21.10% | 758.954 |
| 13 | 20.386 | 4.35286 | 17.50% | 640.608 |
| 14 | 21.914 | 4.05261 | 24.20% | 803.125 |
| 15 | 22.640 | 3.92439 | 9.60% | 421.049 |
| 16 | 23.867 | 3.72533 | 6.30% | 335.668 |
| 17 | 24.553 | 3.62272 | 5.40% | 315.159 |
| 18 | 24.806 | 3.58629 | 6.50% | 343.087 |
| 19 | 25.580 | 3.47959 | 44.40% | 1327.10 |
| 20 | 25.988 | 3.42591 | 11.80% | 473.421 |
| 21 | 27.147 | 3.28222 | 12.90% | 486.080 |
| 22 | 27.715 | 3.21613 | 9.70% | 395.792 |
| 23 | 28.521 | 3.12708 | 4.30% | 249.149 |
| 24 | 29.135 | 3.06256 | 8.00% | 344.276 |
| 25 | 29.638 | 3.01175 | 2.10% | 183.706 |
| 26 | 30.569 | 2.92211 | 3.20% | 206.383 |
| 27 | 31.125 | 2.87113 | 3.10% | 202.852 |
| 28 | 31.799 | 2.81180 | 5.30% | 256.503 |
| 29 | 32.789 | 2.72916 | 1.20% | 139.579 |
| 30 | 33.855 | 2.64562 | 2.60% | 169.028 |
| 31 | 34.827 | 2.57393 | 1.40% | 129.355 |
| 32 | 36.782 | 2.44153 | 4.80% | 216.242 |
| 33 | 38.522 | 2.33512 | 1.60% | 124.831 |
| 34 | 39.646 | 2.27149 | 1.40% | 126.875 |

In some embodiments of the present disclosure, the differential scanning calorimetry curve of the above crystal form A has a peak value of an endothermic peak at 115.37° C.±3° C.

In some embodiments of the present disclosure, the DSC curve of the above crystal form A is shown in FIG. 2.

In some embodiments of the present disclosure, the thermogravimetric analysis curve of the above crystal form A has a weight loss of up to 5.379% at 150.0±3° C.

In some embodiments of the present disclosure, the TGA curve of the above crystal form A is shown in FIG. 3.

The present disclosure also provides a method of preparing the crystal form A of a compound of formula (II), including:

(II)

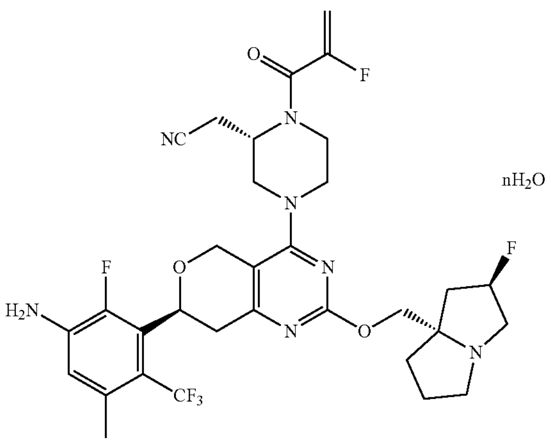

(a) adding a compound of formula (I) to ethanol, and stirring the mixture until clear;
(b) slowly adding water to the system while stirring, and adding seed crystals at 20 to 30° C.;
(c) stirring at 20 to 30° C. for 15 hours;
(d) slowly adding dropwise water into the reaction system at 20 to 30° C., and further stirring for 1 to 3 hours;
(e) filtering, and collecting a solid.

The present disclosure also provides use of the above compound and the crystal form A thereof in the manufacture of a medicament for the treatment of solid tumors.

In some embodiments of the present disclosure, the above solid tumors are lung cancer and rectal cancer.

Technical Effect

The compound of the present disclosure has good cell proliferation inhibitory activity on KRASG12C-mutated MIA-PA-CA-2 cell line and NCI-H358 cells. The compound of the present disclosure has good stability in liver microsomes, hepatocytes, plasma and whole blood, as well as good PK properties and significant anti-tumor effect. The crystal form A is stable, less affected by light and heat, and has good PK properties.

Definition and Description

Unless otherwise specified, the following terms and phrases used herein are intended to have the following meanings. A specific phrase or term should not be considered indefinite or unclear in the absence of a particular definition, but should be understood in the conventional sense. When a trade name appears herein, it is intended to refer to its corresponding commodity or active ingredient thereof.

The intermediate compounds of the present disclosure can be prepared by a variety of synthetic methods well known to those skilled in the art, including the specific embodiments listed below; the embodiments formed by combining the specific embodiments listed below with other chemical synthetic methods, and the equivalent alternative methods well known to those skilled in the art. The alternative embodiments include, but are not limited to, the examples of the present disclosure.

The chemical reactions in the specific embodiments of the present disclosure are completed in a suitable solvent, which must be suitable for the chemical changes of the present disclosure and the reagents and materials required. In order to obtain the compound of the present disclosure, it is sometimes necessary for those skilled in the art to modify or select synthetic steps or reaction schemes based on the existing embodiments.

The present disclosure will be described in detail below through examples, which are not intended to limit the present disclosure in any way.

All solvents used in the present disclosure are commercially available and can be used without further purification.

The structures of compounds disclosed herein can be confirmed by conventional methods well known to those skilled in the art. If the present disclosure relates to an absolute configuration of a compound, the absolute configuration can be confirmed by conventional techniques in the art, such as single-crystal X-Ray diffraction (SXRD). In the single-crystal X-Ray diffraction (SXRD), the diffraction intensity data of the cultivated single crystal is collected using a Bruker D8 venture diffractometer with a light source of CuKα radiation in a scanning mode of φ/ω scan: after collecting the relevant data, the crystal structure is further analyzed by the direct method (Shelxs97) to confirm the absolute configuration.

Compounds are named according to general naming principles in the art or by ChemDraw® software, and commercially available compounds are named with their vendor directory names.

X-Ray Powder Diffraction (XRPD) Method Used in the Present Disclosure

Instrument model: Bruker D2 Phaser X-ray diffractometer

Test method: About 10 to 20 mg of sample was used for XRPD detection.

Detailed XRPD parameters were as follows:

Light tube: Cu, kα, (λ=1.54184 Å).

Voltage of the light tube: 30 kV, current of the light tube: 10 mA

Divergence slit: 0.60 mm

Detector slit: 5.827 mm

Anti-scatter slit: 0 mm

Range of scanning: 3-40 deg

Step size: 0.02 deg

Step length: 0.2 seconds

Differential Scanning Calorimetry (DSC) Method Used in the Present Disclosure

Instrument model: NETZSCH DSC 214 DSC21400A-0958-L

Test method: Sample (about 4.02 mg) was placed in a DSC aluminum pot for testing. Under a condition of 50 mL/min of N2, the sample was heated from 30° C. (room temperature) to 400° C. at a heating rate of 10° C./min.

Thermogravimetric Analysis (TGA) Method Used in the Present Disclosure

Instrument model: TA Discovery TGA 5500 thermogravimetric analyzer

Test method: Sample (2 to 5 mg) was placed in a TGA platinum pot for testing. Under a condition of 25 mL/min of N2, the sample was heated from room temperature to 350° C. or to a weight loss of 20% at a heating rate of 10° C./min.

Single-Crystal X-Ray Diffraction Method Used in the Present Disclosure

Instrument model: Bruker D8 VENTURE CMOS Photon II diffractometer with helios mx multilayer monochrmator.

Test method: 0.0133 g of crystal form A of the compound of formula (II) was dissolved in 2 mL of acetonitrile at room temperature. The sample solution was added into a 4 mL semi-sealed sample vial and was evaporated slowly at room temperature. Colorless massive crystals were obtained after ten days. Temperature of the diffraction experiment was T=173 (2) K.

Instrument parameters:

Bruker D8 VENTURE CMOS Photon II diffractometer with helios mx multilayer monochrmator.

Cryogenic system: Oxford Cryostream 800

Cu: $\lambda$=1.54184 Å, 2.5 kW,

Distance from the crystal to detector: d=45 mm

Tube Voltage: 50 kV

Tube Current: 50 mA

DETAILED DESCRIPTION

Figure 1:
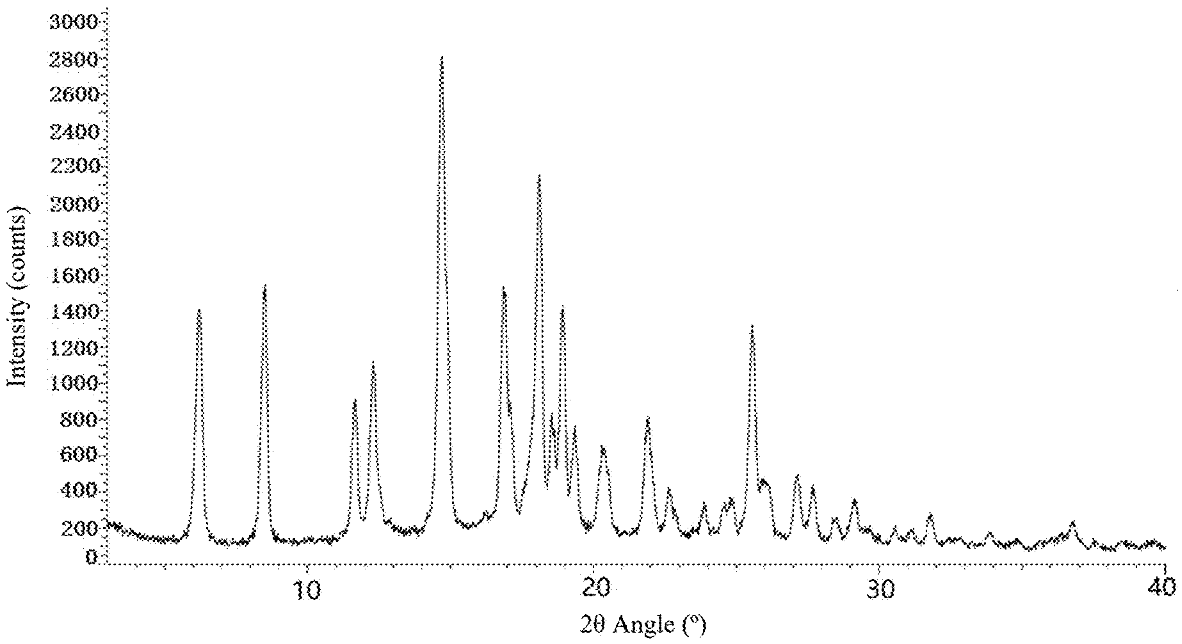
FIG. 1 is the XRPD pattern of the crystal form A of the compound of formula (II) using Cu-K$\alpha$ radiation.

In order to better understand the content of the present disclosure, the present disclosure is further illustrated below in conjunction with specific examples, but the specific examples are not intended to limit the content of the present disclosure.

Example 1: Preparation of the Compound of Formula (I)

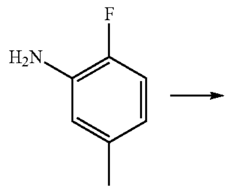

1-1

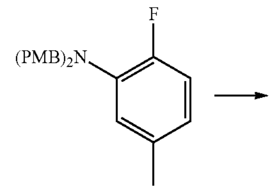

1-2

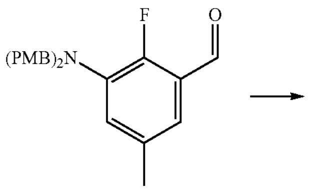

1-3

-continued

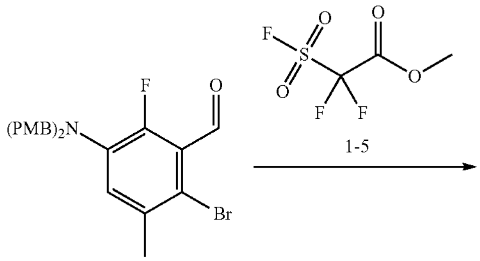

1-4

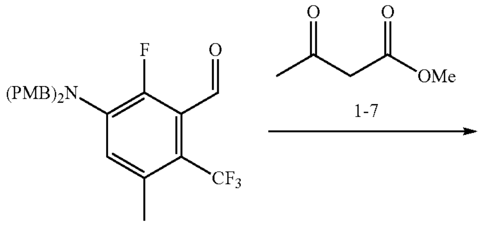

1-6

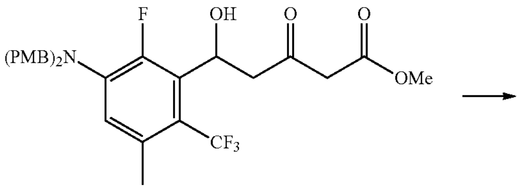

1-8

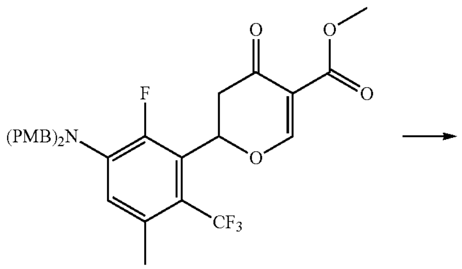

1-9

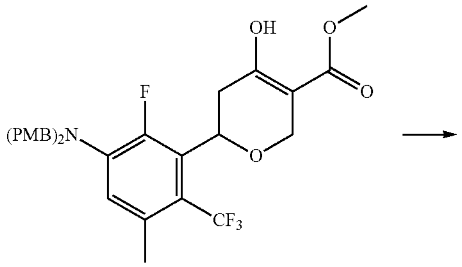

1-10

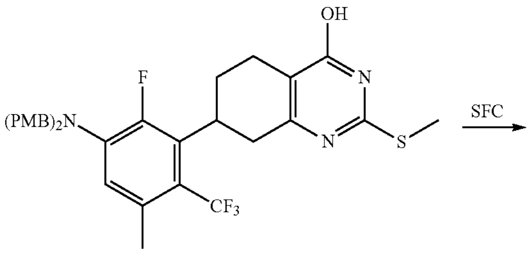

1-11

-continued
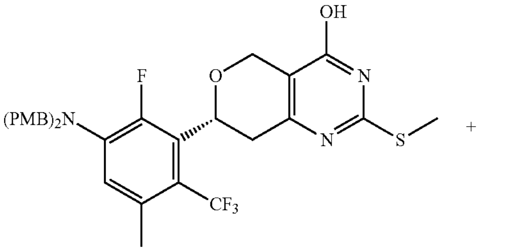
1-12A
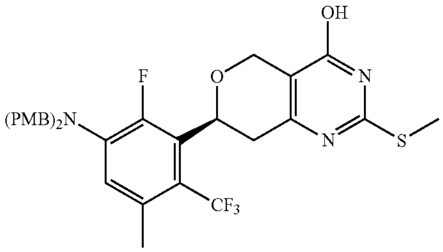
1-12B
1-12B
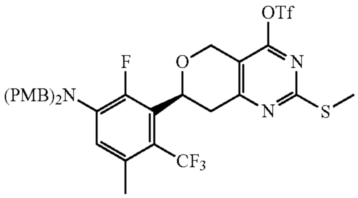
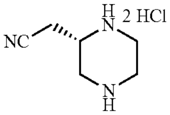
1-14
1-13
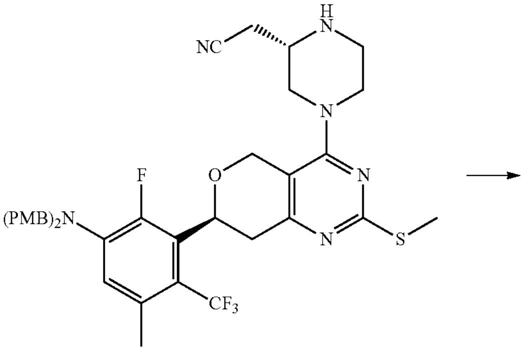
1-15
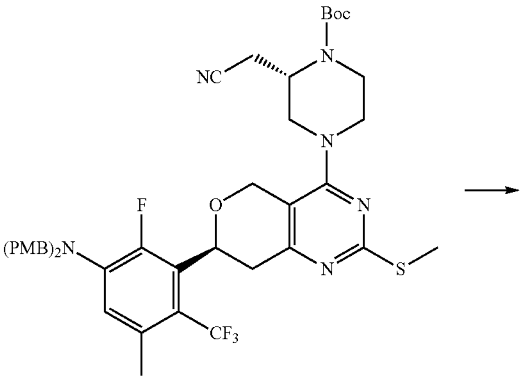
1-16
-continued
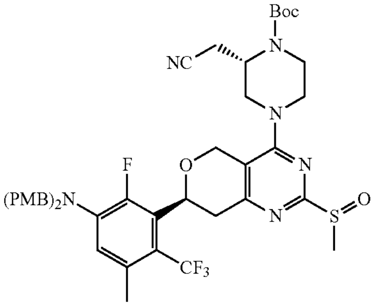
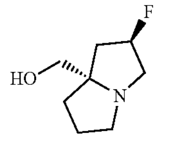
1-18
1-17
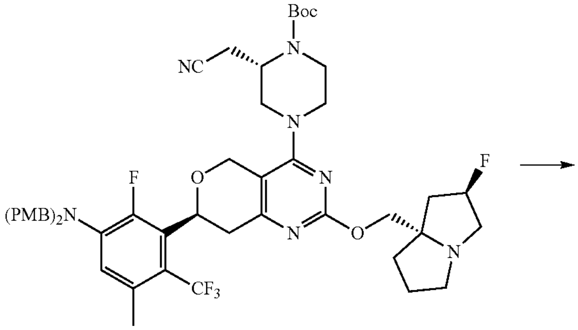
1-19
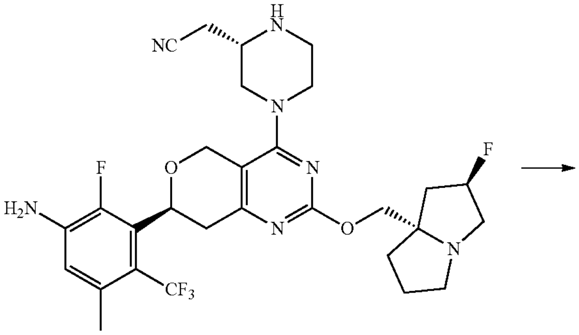
1-20
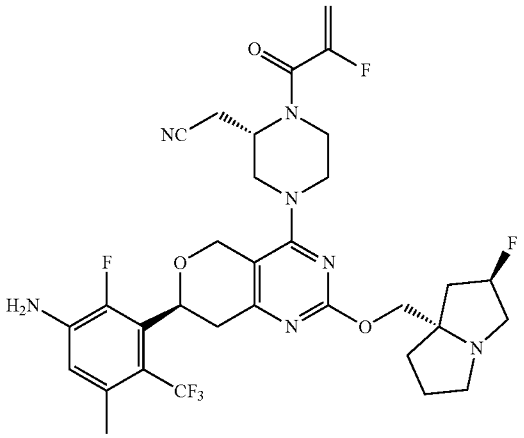
(I)
Step 1: Synthesis of Compound 1-2
A 5-liter three-necked flask was prepared, in which compound 1-1 (250 g, 2.00 mol, 1 eq), anhydrous potassium carbonate (690.26 g, 4.99 mol, 2.5 eq), and potassium iodide (331.62 g, 2.00 mol, 1 eq) were added into N-methylpyrrolidone (2.5 L). Then, p-methoxybenzyl chloride (641.36 g, 4.10 mol, 557.71 mL, 2.05 eq) was added dropwise, and the reaction solution was yellow and turbid. The resulting mixture was stirred and reacted under nitrogen in an oil bath at 120° C. for 5 hours. 6 batches of the reaction solution (250×6) were combined and added into 20 liters of water. Then, 10 liters of methyl tert-butyl ether was added, and the mixture was stirred. After liquid separation, the organic phase was collected, and the aqueous phase was extracted with methyl tert-butyl ether (5 L×1). The organic phases were combined, washed with saturated brine (10 L×2), dried over anhydrous sodium sulfate, and concentrated under reduced pressure to give a crude product of compound 1-2. 3 liters of petroleum ether was added to the crude product, and the mixture was slurried overnight. The slurry system was milky white and turbid, and filtered through a Buchner funnel. The filter cake was washed with petroleum ether (500 mL×3) to give compound 1-2 from the filter cake. 1H NMR (400 MHz, $CDCl_3$) δ=7.23-7.18 (m, 4H), 6.91-6.87 (m, 1H), 6.82-6.76 (m, 4H), 6.65-6.59 (m, 2H), 4.20 (s, 4H), 3.79 (s, 6H), 2.19 (s, 3H). LCMS: MS m/z=366.1 $[M+H]^+$.

Step 2: Synthesis of Compound 1-3

2,2,6,6-tetramethylpiperidine (2.44 kg, 17.29 mol, 2.94 L, 4 eq) was added to anhydrous tetrahydrofuran (15 L), and the mixture was cooled to −5 to 0° C. The system was purged with nitrogen three times, and n-butyllithium (2.5 M, 6.92 L, 4 eq) was added dropwise under nitrogen. The mixture was reacted at −5 to 0° C. for 15 minutes, and cooled to −60° C. A solution of compound 1-2 (1.58 kg, 4.32 mol, 1 eq) in tetrahydrofuran (1.5 L) was added dropwise. After the dropwise addition was completed, the mixture was reacted at −65 to −60° C. for 0.5 hours. Then, N,N-dimethylformamide (3.16 kg, 43.24 mol, 3.33 L, 10 eq) was quickly added, and the mixture was reacted at −60° C. for 10 minutes. 20 L of saturated ammonium chloride was added to the reaction solution, and the mixture was extracted with 5 L of methyl tert-butyl ether. The layers were separated. The organic phase was washed with 20 L of saturated ammonium chloride. Then, the aqueous phase was extracted with 10 L of methyl tert-butyl ether. The layers were separated. The organic phases were combined, washed with saturated brine (12 L×2), dried over anhydrous sodium sulfate, filtered, and concentrated. Then, the crude product was slurried with petroleum ether and methyl tert-butyl ether (3/1, 3 L) for 5 hours, and then filtered. The filter cake was collected to give compound 1-3. $^1H$ NMR (400 MHz, $CDCl_3$) δ=10.43-10.35 (m, 1H), 7.21-7.18 (m, 5H), 6.92-6.81 (m, 5H), 4.25 (s, 4H), 3.80 (s, 6H), 2.23 (s, 3H). LCMS:MS m/z=394.2$[M+H]^+$.

Step 3: Synthesis of Compound 1-4

Compound 1-3 (1.17 kg, 2.83 mol, 95% purity, 1 eq) was added to N,N-dimethylformamide (5.7 L), and bromosuccinimide (603.35 g, 3.39 mol, 1.2 eq) was added in batches at 5° C. The mixture was reacted at 5 to 15° C. for 1 hour. 5.7 L of water was slowly added to the reaction solution, and a solid was precipitated. After stirring for 20 minutes, 11.4 L of water was slowly added. The mixture was further stirred for 40 min and filtered. The filter cake was washed with water (2 L×2). The crude product was slurried with 7.7 L of a mixed solvent of petroleum ether and methyl tert-butyl ether (10:1) for 12 hours, and then filtered. The filter cake was washed with 500 mL of a mixed solvent of petroleum ether and methyl tert-butyl ether (10:1). After vacuum concentration, the product was blown with nitrogen for 12 hours to give compound 1-4. $^1H$ NMR (400 MHz, $CDCl_3$) δ=10.39 (s, 1H), 7.17 (d, J=8.8 Hz, 4H), 6.89 (d, J=8.8 Hz, 1H), 6.85-6.82 (m, 4H), 4.22 (s, 4H), 3.79 (s, 6H), 2.28 (s, 3H). LCMS:MS m/z=472.1$[M+H]^+$, 474.1$[M+H]^+$.

Step 4: Synthesis of Compound 1-6

Compound 1-4 (130 g, 275.22 mmol, 1 eq), ketone iodide (104.83 g, 550.44 mmol, 2 eq) and compound 1-5 (264.37 g, 1.38 mol, 175.08 mL, 5 eq) were dissolved in DMF (1.3 L). The mixture was stirred at 100° C. under nitrogen for 4 hours. The reaction system was cooled down, filtered, and poured into water (1.3 L) to quench the reaction. The mixture was extracted with methyl tert-butyl ether (400 mL×2), washed with saturated brine (300 mL), dried over anhydrous sodium sulfate, and filtered. Mother liquor was collected and concentrated to give a crude product. The crude product was slurried with petroleum ether and methyl tert-butyl ether (8/1, 300 mL) to give compound 1-6. Mother liquor was collected, concentrated, and purified with column chromatography (petroleum ether/ethyl acetate=100/1 to 5/1) to give a crude product. The crude product was slurried with petroleum ether and methyl tert-butyl ether (8/1,100 mL) to give compound 1-6. The two batches of solid were mixed, slurried with petroleum ether, and filtered. A solid was collected to give compound 1-6. $^1H$ NMR (400 MHz, $CDCl_3$) δ=10.37 (q, J=4.0 Hz, 1H), 7.18-7.11 (m, 4H), 6.89-6.82 (m, 4H), 6.73 (d, J=8.8 Hz, 1H), 4.36 (s, 4H), 3.81 (s, 6H), 2.37-2.29 (m, 3H). LCMS: MS m/z=484.0$[M+Na]^+$.

Step 5: Synthesis of Compound 1-8

Sodium hydrogen (70.21 g, 1.76 mol, 60% purity, 1.8 eq) was added to anhydrous tetrahydrofuran (4.5 L) and cooled to −5° C. The mixture was purged with nitrogen three times, and compound 1-7 (203.82 g, 1.76 mol, 188.72 mL, 1.8 eq) was added dropwise under nitrogen. The mixture was reacted at −5 to 0° C. for 10 minutes, and then n-butyllithium (2.5 M, 702.14 mL, 1.8 eq) was added dropwise. The mixture was reacted at −5 to 0° C. under nitrogen for another 10 minutes and cooled to −10° C. A solution of compound 1-6 (450 g, 975.19 mmol, 1 eq) in tetrahydrofuran (450 mL) was added dropwise, and the mixture was reacted at −10° C. for 10 minutes. The reaction solution was slowly added to 5 L of saturated ammonium chloride for extraction. The layers were separated. The organic phase was washed with 4 L of saturated brine, dried over anhydrous sodium sulfate, filtered, and concentrated. 900 mL×4 of petroleum ether was added to the concentrated crude product to wash with shaking. The petroleum ether supernatant was poured off, and the crude product was concentrated in vacuum to give compound 1-8. $^1H$ NMR (400 MHz, $CDCl_3$) δ=7.18-7.15 (m, 4H), 6.90-6.78 (m, 4H), 6.61 (d, J=8.8 Hz, 1H), 5.72-5.57 (m, 1H), 4.31 (m, 4H), 3.81 (s, 6H), 3.76 (s, 3H), 3.56 (s, 2H), 3.50-3.38 (m, 1H), 2.98-2.93 (m, 1H), 2.38-2.26 (m, 3H). LCMS: MS m/z=578.1$[M+H]^+$.

Step 6: Synthesis of Compound 1-9

Compound 1-8 (1.15 kg, 1.77 mol, 89% purity, 1 eq) was added to dichloromethane (5.7 L), and N,N-dimethylformamide dimethyl acetal (337.86 g, 2.84 mol, 376.66 mL, 1.6 eq) was added. The mixture was reacted at 25° C. for 1 hour, and cooled to 0° C. Boron trifluoride-diethyl ether (377.27 g, 2.66 mol, 328.06 mL, 1.5 eq) was added dropwise at 0 to 5° C., and the mixture was reacted for 10 minutes. Showed by LCMS, the starting materials disappeared and Ms signal of product appeared. The reaction solution was slowly added to 10 L of semi-saturated sodium bicarbonate solution for extraction. The layers were separated. The organic phase was washed with 5 L of saturated brine, dried over anhydrous sodium sulfate, filtered, and concentrated. The crude product was divided evenly into six parts, and in each part, 0.83 L of methyl tert-butyl ether was added. The mixture was stirred for 20 minutes and a solid was precipitated. 0.5 L of a mixed solvent of petroleum ether and methyl tert-butyl ether (1:1) was added, and the mixture was slurried overnight for 16 hours. The six parts were filtered together. The filter cake was rinsed with a mixed solvent of petroleum ether and methyl tert-butyl ether (1:1, 800 mL×2) and rotary evaporated to dryness. Mother liquor was purified with column chromatography (petroleum ether:ethyl acetate=100:0-0:1) to give compound 1-9. $^1$H NMR (400 MHz, $CDCl_3$) δ=8.43 (d, J=0.8 Hz, 1H), 7.21-7.10 (m, 4H), 6.91-6.81 (m, 4H), 6.70 (d, J=8.8 Hz, 1H), 5.93 (dd, J=3.2, 14.8 Hz, 1H), 4.35 (s, 4H), 3.8 (s, 3H), 3.81 (s, 6H), 3.38-3.29 (m, 1H), 2.68 (dd, J=3.6, 16.8 Hz, 1H), 2.39-2.24 (m, 3H). LCMS: MS m/z=588.2[M+H]$^+$.

Step 7: Synthesis of Compound 1-10

Compound 1-9 (775 g, 1.32 mol, 1 eq) was added to tetrahydrofuran (4 L). The mixture was cooled to −60° C. and purged with nitrogen three times. Then, tri-sec-butylborohydride (1M, 1.45 L, 1.1 eq) was added dropwise under nitrogen. The mixture was reacted at −60° C. for 10 minutes. The reaction solution was slowly added to 3.5 L of 1M hydrochloric acid solution, and 2 L of water was added for extraction. The layers were separated. The aqueous phase was further extracted with 2 L of ethyl acetate. The organic phases were combined, and 1 L of ethyl acetate was added. The mixture was washed with 5 L of saturated brine, dried over anhydrous sodium sulfate, filtered, and concentrated. The crude product was divided into 4 parts, and in each part, 200 mL of methyl tert-butyl ether was added, respectively. The mixture was stirred for 10 min, and 200 mL of petroleum ether was slowly added. After stirring for 0.5 to 1 hour, a solid was precipitated. 1.6 L of petroleum ether was further added in batches, and the mixture was slurried for 12 hours. The slurry was filtered, and the filter cake was washed 3 times with 300 mL of a mixed solvent of petroleum ether and methyl tert-butyl ether (10:1). A solid was collected to give compound 1-10 (1.15 kg). $^1$H NMR (400 MHz, $CDCl_3$) δ=7.167-7.14 (m, 4H), 6.87-6.83 (m, 4H), 6.63 (d, J=8.8 Hz, 1H), 5.05-5.00 (m, 1H), 4.61-4.58 (m, 1H), 4.42-4.24 (m, 5H), 3.85-3.73 (m, 10H), 3.13-3.05 (m, 1H), 2.47-2.38 (m, 1H), 2.35-2.31 (m, 3H). LCMS: MS m/z=590.3. [M+H]$^+$.

Step 8: Synthesis of Compound 1-11

Compound 1-10 (310 g, 525.80 mmol, 1 eq) was added to ethanol (1.55 L). Then, S-methylisothiourea sulfate (439.11 g, 1.58 mol, 3 eq) and sodium carbonate (111.46 g, 1.05 mol, 2 eq) were added. The mixture was reacted at 45 to 50° C. (internal temperature) under nitrogen for 16 hours. Most of the ethanol was removed by concentration. 500 ml of water and 400 ml of ethyl acetate were added to the crude product. The mixture was stirred, and adjusted to a pH of 3 to 4 with 500 ml of 1M hydrochloric acid. An off-white solid was precipitated. 600 ml of petroleum ether was further added. With stirring, a large amount of off-white solid was precipitated in the system. The system was filtered through a Buchner funnel, and the filter cake was washed with ethyl acetate (200 mL×2) to give a filter cake as a product. The filter cake was dissolved in 2 L of dichloromethane. After liquid separation, the organic phase was dried over anhydrous sodium sulfate, and concentrated to give compound 1-11. $^1$H NMR (400 MHz, $CDCl_3$) δ=7.22-7.14 (m, 4H), 6.91-6.82 (m, 4H), 6.65 (dd, J=8.4 Hz 1H), 5.12-5.08 (m, 1H), 4.97-4.91 (m, 1H), 4.67-4.57 (m, 1H), 4.45-4.22 (m, 4H), 3.88-3.74 (m, 6H), 3.43-3.35 (m, 1H), 2.77-2.72 (m, 1H), 2.59 (m, 3H), 2.40-2.31 (m, 3H). LCMS:MS m/z=630.2[M+H]$^+$.

Step 9: Synthesis of Compound 1-12B

Compound 1-11 was separated by SFC (column: DAICEL CHIRALPAK AD (250 mm*50 mm, 10 μm); mobile phase: [0.1% $NH_3$. $H_2O$ EtOH]; EtOH %: 45%-45%, 6.3 min) to give compound 1-12B (peak time: 1.665 min) and compound 1-12A (peak time: 2.446 min).

Step 10: Synthesis of Compound 1-13

Compound 1-12B (2 g, 3.18 mmol, 1 eq) was dissolved in dichloromethane (20 mL), and N,N-diisopropylethylamine (1.23 g, 9.53 mmol, 1.66 mL, 3 eq) was added. The mixture was cooled to 0 to 10° C., and trifluoromethanesulfonic anhydride (1.34 g, 4.76 mmol, 786.11 μL, 1.5 eq) was slowly added into the system. The mixture was reacted at this temperature for 15 minutes. Saturated aqueous ammonium chloride solution (15 mL) was added. After liquid separation, the aqueous phase was extracted with dichloromethane (15 mL×2). The organic phases were combined, dried over anhydrous sodium sulfate, filtered, and concentrated to give a crude product. The crude product was separated by column chromatography (petroleum ether/ethyl acetate=100/1 to 0/1) to give compound 1-13. LCMS m/z=762.2[M+H]$^+$. $^1$H NMR (400 MHz, $CDCl_3$) δ=7.21-7.11 (m, 4H), 6.90-6.80 (m, 4H), 6.66 (d, J=8.4 Hz, 1H), 5.19-5.15 (m, 1H), 5.04-4.93 (m, 1H), 4.77-4.72 (m, 1H), 4.41-4.19 (m, 4H), 3.80 (s, 6H), 3.62-3.54 (m, 1H), 3.11-2.97 (m, 1H), 2.56 (s, 3H), 2.42-2.31 (m, 3H). LCMS:MS m/z=762.2[M+H]$^+$.

Step 11: Synthesis of Compound 1-15

Compound 1-13 (147 g, 186.74 mmol, 96.767% purity, 1 eq) was dissolved in N,N-dimethylformamide (1.5 L). N,N-diisopropylethylamine (72.40 g, 560.23 mmol, 97.58 mL, 3 eq) was added, and then compound 1-14 (42.54 g, 214.76 mmol, 1.15 eq, 2HCl) was also added. The mixture was heated to 50° C. and stirred for 0.5 hours to give a solution of compound 1-15 in N,N-dimethylformamide. The reaction solution was directly used in the next step.

Step 12: Synthesis of Compound 1-16

A solution of compound 1-15 (137.8 g, 187.02 mmol, 1 eq) in N,N-dimethylformamide (1.5 L) was added into a stirrer, and triethylamine (18.92 g, 187.02 mmol, 26.03 mL, 1 eq) was added. Then, di-tert-butyl dicarbonate (48.98 g, 224.42 mmol, 51.56 mL, 1.2 eq) was added to the reaction solution, and the mixture was stirred at 18° C. for 10 hours. After pouring the mixture into water (1.5 L), ethyl acetate (400 mL×3) and saturated aqueous ammonium chloride solution (400 mL×4) were added. The organic phase was dried over anhydrous sodium sulfate, filtered, and concentrated to give compound 1-16. $^1$H NMR (400 MHz, $CDCl_3$) δ=7.16 (d, J=8.4 Hz, 4H), 6.85 (d, J=8.6 Hz, 4H), 6.64 (d, J=8.0 Hz, 1H), 5.22 (d, J=7.2 Hz, 1H), 4.90-4.68 (m, 2H), 4.61 (s, 1H), 4.41-4.21 (m, 4H), 4.04 (s, 1H), 3.80 (s, 6H), 3.71 (s, 1H), 3.50 (d, J=11.0 Hz, 2H), 3.30 (s, 1H), 3.24-3.02 (m, 2H), 2.90 (d, J=2.0 Hz, 1H), 2.78-2.58 (m, 2H), 2.55 (s, 3H), 2.34 (d, J=4.0 Hz, 3H), 1.51 (s, 9H). LCMS m/z=837.2 $[M+H]^+$.

Step 13: Synthesis of Compound 1-17

Compound 1-16 (245 g, 278.10 mmol, 95% purity, 1 eq) was dissolved in anhydrous dichloromethane (2500 mL), and cooled to 0 to 10° C. Then, m-chloroperoxybenzoic acid (56.46 g, 278.10 mmol, 85% purity, 1 eq) was added in batches, and the mixture was stirred at 10° C. for 0.5 hours. Additional m-chloroperoxybenzoic acid (8.47 g, 41.71 mmol, 85% purity, 0.15 eq) was added, and the mixture was stirred at 10° C. for another 0.5 hours. This reaction was processed together with a batch of 10 g of compound 1-16. The reaction solution was washed with saturated sodium bicarbonate (1500 mL), 5% sodium thiosulfate (1500 mL) (after passing the test with a wet starch potassium iodide test paper), and half-saturated brine (1500 mL). The organic phase was dried over anhydrous sodium sulfate, filtered, concentrated, and purified with column chromatography (ethyl acetate:petroleum ether=10%-15%-20%-30%) to give compound 1-17. $^1$HNMR (400 MHz, $CDCl_3$) δ ppm 7.15 (d, J=8.00 Hz, 4H), 6.85 (d, J=8.80 Hz, 4H), 6.65 (d, J=8.80 Hz, 1H), 5.27 (m, 1H), 4.78-4.91 (m, 2H), 4.61 (s, 1H), 4.24-4.38 (m, 4H), 3.90-4.18 (m, 2H), 3.78-3.82 (m, 6H), 3.42-3.70 (m, 3H), 3.33 (br s, 1H), 3.06-3.28 (m, 2H), 2.90 (s, 3H), 2.66 (m, 2H), 2.29-2.41 (s, 3H), 1.51 (s, 9H). LCMS m/z=853.2$[M+H]^+$.

Step 14: Synthesis of Compound 1-19

Compound 1-18 (18.24 g, 114.59 mmol, 1.2 eq) was dissolved in anhydrous tetrahydrofuran (900 mL), and the mixture was cooled to −20° C. Then, sodium tert-butoxide (11.01 g, 114.59 mmol, 1.2 eq) was added, and the mixture was stirred for 15 minutes. Then, a solution of compound 1-17 (90.5 g, 95.49 mmol, 90% purity, 1 eq) in anhydrous tetrahydrofuran (180 mL) was added, and the mixture was further stirred for 0.5 h. This reaction was processed together with a batch of 50 g of compound 1-18. 1000 mL of saturated ammonium chloride was added to the reaction solution to quench the reaction. After liquid separation, the aqueous phase was extracted with ethyl acetate (1000 mL). The layers were separated. The organic phase was dried over anhydrous sodium sulfate, filtered, concentrated, and purified by column chromatography (ethyl acetate:petroleum ether=20%-50%-100%) to give compound 1-19 as a white solid. LCMS m/z=948.4$[M+H]^+$.

Step 15: Synthesis of Compound 1-20

Compound 1-19 (97.00 g, 97.20 mmol, 95% purity, 1 eq) was dissolved in 2-methyltetrahydrofuran (500 mL), and the mixture was cooled to 0° C. Then, hydrochloric acid (8 M, 614.80 mL, 50.6 eq) was added dropwise to the reaction solution, and the mixture was heated to 25° C. and stirred for 2 hours. Then, n-heptane (200 mL) was added, and the layers were separated. The aqueous phase was collected, and 2-methyltetrahydrofuran (300 mL) was added. pH of the mixture was adjusted to 8 to 9 with sodium carbonate, and the mixture was stirred until clear. After liquid separation, the organic phase was collected, and the aqueous phase was extracted with 2-methyltetrahydrofuran (300 mL×2). The organic phase was collected, washed with saturated brine (200 mL), dried over anhydrous magnesium sulfate, and filtered. The organic phase was collected and concentrated to give a crude product. The crude product was dissolved in dichloromethane (1000 mL), and trifluoroacetic acid (283.73 g, 2.49 mol, 184.24 mL, 25.6 eq) was slowly added to dichloromethane, while keeping the temperature below 10° C. The mixture was stirred at 25° C. for 3 hours. The reaction solution was poured into 500 mL of ice water, and the mixture was stirred until clear. After liquid separation, the organic phase was extracted with water (300 mL×3). The two batches of aqueous phase were combined, and then extracted with dichloromethane (500 mL×4). The organic phase was discarded. The aqueous phase was cooled to 10° C., in which 500 mL of 2-methyltetrahydrofuran was added (leading to heat generation). Then, pH of the mixture was adjusted to 9 with sodium carbonate, and 2-methyltetrahydrofuran (400 mL×2) was added for extraction. The organic phases were combined, washed respectively with water (300 mL×4) and saturated brine (300 mL), dried over anhydrous sodium sulfate, filtered, and concentrated to give compound 1-20 as a gray solid. LCMS m/z=608.27$[M+H]^+$.

Step 16: Synthesis of Compound of Formula (I)

Compound 1-20 (58 g, 84.00 mmol, 88% purity, 1 eq), N,N-diisopropylethylamine (21.71 g, 168.00 mmol, 29.26 mL, 2 eq), and 2-(7-azabenzotriazol)-N,N,N',N'-tetramethyluronium hexafluorophosphate (38.33 g, 100.80 mmol, 1.2 eq) were dissolved in DMF (600 mL), and then the mixture was cooled to 0° C. 2-fluoroacrylic acid (6.81 g, 75.60 mmol, 0.9 eq) was added in batches, and the mixture was stirred at 0° C. for 10 min. The reaction solution was poured into 900 mL of water, and then extracted with ethyl acetate (200 mL×3). The organic phases were combined, washed with saturated ammonium chloride (200 mL×3), saturated sodium carbonate (200 mL×3), and saturated brine (200 mL), respectively, and then dried over anhydrous sodium sulfate, filtered, and concentrated. Then the mixture was slurried with acetonitrile and water (100 mL: 150 mL) for 16 hours. The slurry was filtered to give the compound of formula (I). SFC analysis method (column: Chiralcel OD-3, 50×4.6 mm I.D., 3 μm; mobile phase: A (CO2) and B (methanol, containing 0.05% diisopropylamine); gradient: B %=5 to 50%, 3 min; flow rate: 3.4 mL/min; wavelength: 220 nm; pressure: 1800 psi, optical purity: 99.21%, peak time: 1.840 min). $^1$H NMR (400 MHz, $CD_3OD$) δ=6.80-6.68 (m, 1H), 5.73-5.51 (m, 1H), 5.46-5.19 (m, 3H), 5.05-4.90 (m, 3H), 4.74-4.58 (m, 2H), 4.37-4.26 (m, 1H), 4.20-4.06 (m, 2H), 4.05-3.84 (m, 3H), 3.79-3.59 (m, 2H), 3.54-3.43 (m, 1H), 3.42-3.35 (m, 1H), 3.31-3.24 (m, 1H), 3.13-2.89 (m, 3H), 2.82-2.52 (m, 2H), 2.50-2.42 (m, 1H), 2.41-2.30 (m, 5H), 2.29-2.18 (m, 1H).

Example 2: Single-Crystal X-Ray Diffraction Analysis of the Compound of Formula (III)

(III)

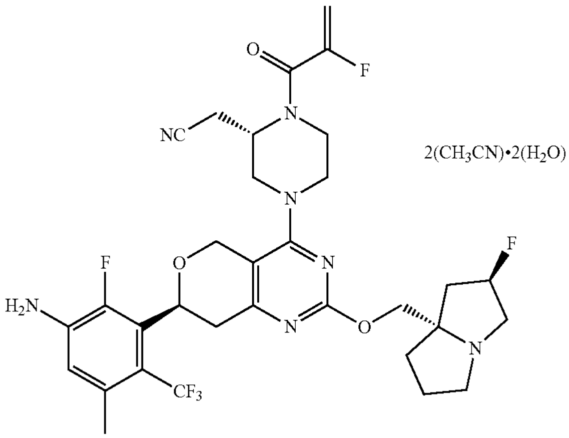

Figure 6:
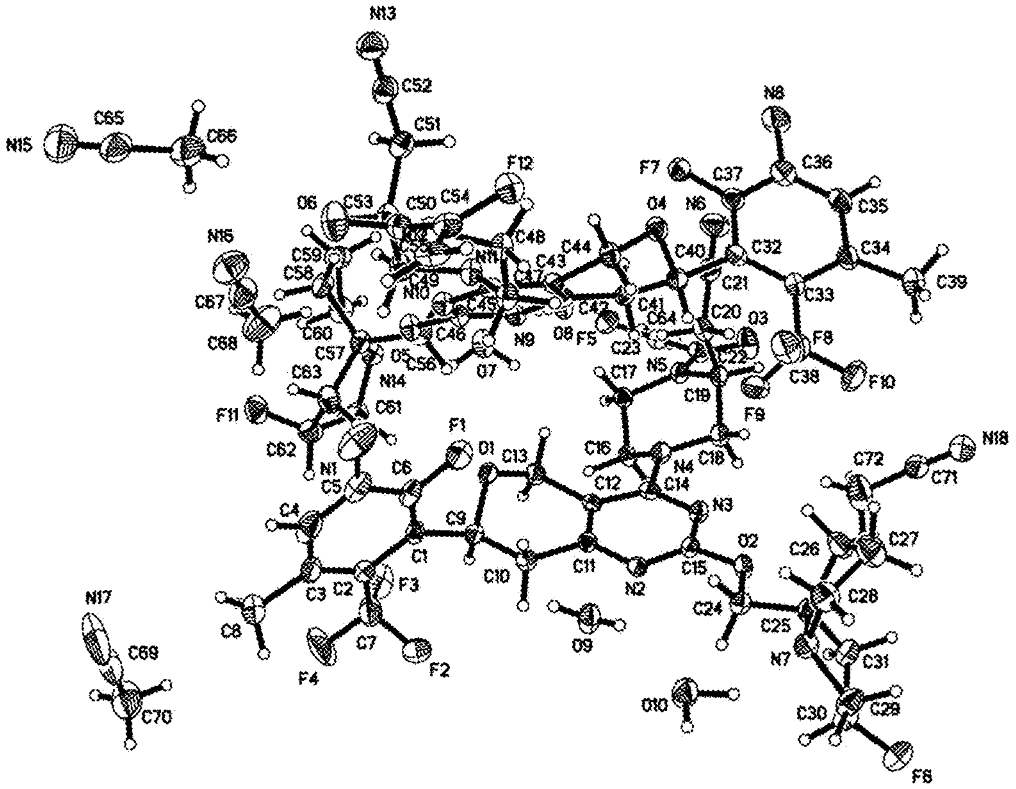
FIG. 6 is an ellipsoid diagram of the three-dimensional structure of the single crystal X-ray diffraction of the compound of formula (III).

$2(CH_3CN)\bullet 2(H_2O)$ 0.0133 g of crystal form A of compound of formula (II) was dissolved in 2 mL of acetonitrile at room temperature. The sample solution was added into a 4 mL semi-sealed sample vial, and evaporated slowly at room temperature. Colorless massive crystals were obtained after ten days. The crystals were collected, and diffraction intensity data was collected using a single-crystal X-ray diffractometer (D8-VENTURE). Crystal structure data of the compound of formula (III) is shown in Table 2, and the ellipsoid diagram of the three-dimensional structure of the compound of formula (III) is shown in FIG. 6.

TABLE 2

| Crystal data of the compound of formula (III) | |
|---|---|
| Crystal Size | 0.180 × 0.160 × 0.120 mm |
| Radiation Type | Cu Kα (λ = 1.54184 Å) |
| Crystal system | Tetragonal |
| Space Group | P4(1) |
| Cell Size | a = 10.9496(3) Å |
| | b = 10.9496(3) Å |
| | c = 64.126(2) Å |
| | α = β = γ = 90° |
| Cell Volume | V = 7688.3 (5) $Å^3$ |
| Cell Formula Units | Z = 8 |
| Crystal Density | $D_c$ = 1.375 $Mg/m^3$ |
| Crystal F(000) | 3328 |
| Absorption Coefficient mu | μ(Cu Kα) = 0.971 $mm^{-1}$ |
| Limiting Indices | −12 ≤ h ≤ 12 |
| | −9 ≤ k ≤ 12 |
| | −75 ≤ l ≤ 73 |
| Cell Measurement Temperature | T = 173 (2) K. |
| Theta range for data collection | 2.756~65.272° |
| Goodness-of-fit on F^2 | 1.028 |
| Final R indices [I>2sigma(I)] | $R_1$ = 0.0718, $wR_2$ = 0.1968 |
| R indices (all data) | $R_1$ = 0.0802, $wR_2$ = 0.2030 |
| Largest diff. peak and hole | 0.310, −0.335e·$Å^{-3}$ |
| Reflections collected/unique | 68300/12934 [$R_{(int)}$ = 0.0906] |

Example 3: Preparation of Crystal Form a of Compound of Formula (II)

Method 1: Compound of formula (I) (0.2 g) was added to ethanol (2.4 mL), and the mixture was heated to 50° C. After dissolving, water (0.48 mL) was slowly added to the reaction solution, and the mixture was stirred at 50° C. for 72 hours. After filtration, a solid was collected to give the crystal form A of compound of formula (II).

Method 2: Compound of formula (I) (5.0 g) was added to ethanol (4 V) and the mixture was stirred until clear. Water (1 V) was slowly added to the system, and seed crystals (0.5 g) were added at 20 to 30° C. The mixture was stirred at this temperature for 15 hours. Then, water (3V) was slowly added dropwise, and the mixture was further stirred for 1 to 3 hours. After filtration, the filter cake was collected to give the crystal form A of compound of formula (II).

Example 4: Solid Stability Assay of Crystal Form a of Compound of Formula (II)

According to the "Guiding Principles for Stability Testing of Raw Materials and Preparations" (Chinese Pharmacopoeia 2015 Edition, Part Four, General Principles, Chapter 9001), crystal stability of the crystal form A of compound of formula (II) was investigated under the conditions of high temperature (60° C., unsealed), high humidity (room temperature/relative humidity 92.5%, unsealed) and strong light (5000 lx, unsealed), as well as long-term experiments (25±2° C./60±5% RH) and accelerated experiments (40±2° C./75±5% RH).

About 20 mg of the crystal form A of compound of formula (II) was weighed and placed at the bottom of a glass sample vial. The sample was spread into a thin layer. For the samples placed under conditions of high temperature and high humidity, the vial mouth was sealed with aluminum foil, and some small holes were punched in the aluminum foil to ensure that the samples were fully in contact with the ambient air. For the samples placed under condition of strong light, the vial mouth was sealed with aluminum foil, and some small holes were punched in the aluminum foil. Samples placed under different conditions were sampled and tested (XRPD) on day 5 and day 10, respectively. The assay results were compared with the initial assay results on day 0. The assay results are shown in Table 3 below.

Crystal form A of compound of formula (II) was put into medicinal double-layer low-density polyethylene bags. Each medicinal low-density polyethylene bag was tied tightly with a tie, and then was placed into a single-layer aluminum foil bag. The single-layer aluminum foil bag was then heat-sealed. Finally, the samples were stored in plastic buckets and stored in a chamber with constant temperature and humidity. The packaging used in the stability assay simulated the material storage packaging. The material was divided into 1.5 g/package as stability samples under red light. Each sample was packaged in the same way and labeled with a stability sample label. The samples placed under different conditions were sampled and tested (XRPD) in the 3rd and 6th months. The assay results were compared with the initial assay results on day 0. The assay results are shown in Table 3 below.

TABLE 3

Solid stability assay results of crystal form A of compound of formula (II)

| Assay conditions | Time point | Crystal form |
|---|---|---|
| — | 0 day | Crystal form A |
| High temperature (60° C., unsealed) | 5 days | Crystal form A |
| | 10 days | Crystal form A |

TABLE 3-continued

| Solid stability assay results of crystal form A of compound of formula (II) | | |
|---|---|---|
| Assay conditions | Time point | Crystal form |
| High humidity (25° C./relative humidity 92.5%, unsealed) | 5 days | Crystal form A |
| | 10 days | Crystal form A |
| Light control*[1] | 5 days | Crystal form A |
| | 10 days | Crystal form A |
| 25 ± 2° C./60 ± 5% relative humidity | 3 months | Crystal form A |
| | 6 months | Crystal form A |
| 40 ± 2° C./75 ± 5% relative humidity | 3 months | Crystal form A |
| | 6 months | Crystal form A |

Light control*[1]: The light control sample needed to be placed at the same time. The light control sample was sealed with a screw cap and then completely wrapped in tin foil.

Conclusion: The crystal form A of compound of formula (II) has good stability under conditions of high temperature, high humidity, strong light, as well as long-term experiments and accelerated experiments.

Biological Assay Data

Assay Example 1: Assay of Inhibitory Effect of Compound on the Proliferation of $KRAS^{G12C}$-Mutated MIA-PA-CA-2 Cells 1.1 Purpose of the Assay Compound was assayed for $IC_{50}$ of inhibition of proliferation of $KRAS^{G12}$C-mutated MIA-PA-CA-2 cells.

1.2 Reagent

The main reagent used in this assay included CellTiter-Glo (Promega, Cat. No. G7573).

1.3 Instrument

The main instrument used in this assay was PerkinElmer EnVision multi-function microplate reader.

1.4 Method of the assay

1) Adherent cells were digested with trypsin to form a cell suspension, and the cell suspension was counted for later use.
2) An appropriate amount of cells was added into a centrifuge tube, and a cell culture medium was added to make up the required volume; then the cells were plated to a 96-well plate at a final density of 2000 cells/well, 100 μL of culture medium.
3) After incubating for 24 hr, the compound was formulated to 10 mM with DMSO, and serially diluted 3-fold with DPBS (Dulbecco's Phosphate Buffered Saline) to 9 points; 10 μL was added to each well in duplicate. 10 μL of DPBS per well was added to the assay control wells (Con).
4) On the same day, 50 μL of CellTiter Glo was added to another cell culture plate without compound, and the fluorescence value was read by EnVision. The value was marked as Day0 value.
5) After 72 h incubation of cells treated with compound, the plate was removed, and 50 μL of CellTiter Glo was added to the cell plate. The fluorescence value was read by EnVision.
6) Data analysis: The inhibition rate of cells in each well was calculated according to the following equation:

$$\text{Inhibition rate } \% = \left(1 - \frac{FCpd}{FCon - FDay0}\right) * 100\%$$

* $F_{Day0}$ was the reading value of the original cell number assay well without compound treatment;

$F_{Con}$ was the fluorescence reading value of the Con group after 72 hr of incubation.

$F_{Cpd}$ was the fluorescence reading value of each compound well after 72 hr of incubation.

7) Log(agonist) vs. response—Variable slope nonlinear fit analysis on the inhibition rate data (inhibition rate %) of compound was performed to give $IC_{50}$ values of compound by GraphPad Prism software using the following equation:

$$Y=\text{Bottom}+(\text{Top}-\text{Bottom})/(1+10\hat{}((\text{Log } IC_{50}-X)*\text{HillSlope}))$$

1.5 Results of the Assay

TABLE 4

| Assay results of compound of the present disclosure on the inhibition of proliferation of $KRAS^{G12C}$-mutated MIA-PA-CA-2 cells | |
|---|---|
| Assay sample | $IC_{50}$ (nM) |
| Compound of formula (I) | 0.44 |

The assay results showed that the compound of formula (I) has good inhibitory activity on cell proliferation of $KRAS^{G12C}$-mutated MIA-PA-CA-2 cell line.

Assay Example 2: Assay of the Inhibitory Effect of Compound on the Proliferation of $KRAS^{G12C}$ Mutated H358 Cells 2.1 Purpose of the Assay Compound was assayed for $IC_{50}$ of inhibition of proliferation of $KRAS^{G12}$C-mutated H358 cells.

2.2 Reagent

The main reagents used in this assay included RPMI-1640 medium, penicillin/streptomycin antibiotics purchased from Vicente, fetal bovine serum purchased from Biosera, Cell-Titer-Glo (cell viability chemiluminescence detection reagent) reagent purchased from Promega, and NCI-H358 cell line purchased from the Cell Bank of the Chinese Academy of Sciences.

2.3 Instrument

The main instrument used in this assay was a Nivo multi-label analyzer (PerkinElmer).

2.4 Method of the assay:

1) NCI-H358 cells were inoculated in a white 96-well plate, and each well contained 80 μL of cell suspension and 4000 NCI-H358 cells. The cell plate was incubated in a carbon dioxide incubator overnight.
2) The compound to be assayed was serially diluted 5-fold with a multi-channel pipette to obtain nine concentrations, i.e., from 2 mM to 5.12 nM. The assay was carried out in duplicate. 78 μL of medium was added to the intermediate plate, and then 2 μL of the serially diluted compound was transferred to each well of the intermediate plate according to the corresponding position. After mixing well, 20 μL per well was transferred to the cell plate. The concentrations of compound transferred to the cell plate ranged from 10 μM to 0.0256 nM. The cell plate was incubated in a carbon dioxide incubator for 5 days. Another cell plate was prepared, and the signal value of the cell plate was read on the day of compound addition as the maximum value (Max value in the equation below) to participate in data analysis. 25 μL of cell viability chemiluminescence detection reagent was added to each well of the cell plate, and the plate was incubated at room temperature for 10 minutes to stabilize the luminescence signal. A multi-label analyzer was used for reading the plate.

3) 25 μL of cell viability chemiluminescence detection reagent was added to each well of the cell plate, and the plate was incubated at room temperature for 10 minutes to stabilize the luminescence signal. A multi-label analyzer was used for reading the plate.

Data Analysis:

The equation (Sample−Min)/(Max−Min)*100% was used to convert the raw data into inhibition rate, and the $IC_{50}$ value can be obtained by curve fitting with four parameters ("log(inhibitor) vs. response—Variable slope" mode in GraphPad Prism). The inhibitory activity of compound of the present disclosure on NCI-H358 cell proliferation was provided in Table 5.

TABLE 5

Assay results of compound of the present disclosure for inhibition of proliferation of $KRAS^{G12C}$-mutated H358 cells

| Assay sample | NCI-H358 $IC_{50}$ (nM) |
|---|---|
| Compound of formula (I) | 0.6 |

Conclusion: Compound of formula (I) exhibits good inhibitory activity on the proliferation of NCI-H358 cells.

Assay Example 3: Metabolic Stability of Hepatocytes

Purpose of the Assay: Metabolic stabilities of assay compound in hepatocytes of CD-1 mice, SD rats, beagle dogs, cynomolgus monkeys, and human were assayed, respectively.

Procedure of the Assay: Several 96-well sample precipitation plates were prepared and named T0, T15, T30, T60, T90, T120, T0-MC, T120-MC and blank substrates, respectively. The recovery medium and incubation medium were taken out in advance and placed in a 37° C. water bath for pre-heating. Cryopreserved hepatocytes were removed from the liquid nitrogen tank and immediately immersed in a 37° C. water bath (approximately 90 seconds). After the cryopreserved hepatocytes had thawed and loosened, they were poured into a centrifuge tube containing 40 mL of recovery medium, and the tube was gently inverted to allow the cells to be resuspended in the recovery medium. The cells were centrifuged at 100×g at room temperature for 5 min, and the supernatant was removed. The hepatocytes were resuspended in an appropriate volume of incubation medium, and the cell viability was calculated by Trypan Blue staining method. 198 μL of hepatocyte suspension ($0.51\times10^6$ cells/mL) was added to the preheated incubation plate. For the culture medium control group, 198 μL of hepatocyte-free incubation medium was added to T0-MC and T120-MC incubation plate. All incubation plates were pre-incubated in a 37° C. incubator for 10 minutes. Then 2 μL of working solutions of the assay sample and the control compound were added, respectively, and the mixture was mixed well. The incubation plate was immediately put into the shaker in the incubator, and the reaction was initiated while starting the timer. For each time point of each compound, 2 duplicate samples were prepared. The incubation conditions were 37° C., saturated humidity, and 5% CO2. In the assay system, the final concentration of the assay sample was 1 μM, the final concentration of the control sample was 3 μM, the final concentration of hepatocytes was $0.5\times10^6$ cells/mL, and the final concentration of the total organic solvent was 0.96%, of which the final concentration of DMSO was 0.10%. At the end of the incubation for the corresponding time point, the incubation plate was taken out, and 25 μL of a mixture of compound and control compound with cells was added to the sample plate containing 125 μL of stop solution (200 ng/mL tolbutamide and labetalol in acetonitrile). For the Blank sample plate, 25 μL of hepatocyte-free incubation medium was added directly. After sealing, all sample plates were shaken on a shaker at 600 rpm for 10 minutes, and then centrifuged at 3220×g for 20 minutes. Supernatants of the assay sample and the control sample were diluted with ultrapure water at a ratio of 1:3. All samples were mixed well and analyzed by LC/MS/MS.

Assay Results: The assay results are shown in Table 6.

TABLE 6

Metabolic stability of the assay compound in hepatocytes of CD-1 mice, SD rats, beagle dogs, cynomolgus monkeys, and human

| Assay sample | Species | $T_{1/2}$ (min) | $CL_{int(hep)}$ (μL/min/$10^6$) | $CL_{int(liver)}$ (mL/min/kg) |
|---|---|---|---|---|
| Compound of formula (I) | CD-1 mice | 9.5 | 146.3 | 1738.1 |
| | SD rats | 20.6 | 67.4 | 315.2 |
| | Cynomolgus monkeys | 27.0 | 51.3 | 184.7 |
| | Beagle dogs | 182.2 | 7.6 | 52.3 |
| | Human | 99.5 | 13.9 | 38.7 |

Conclusion: Metabolic assay in hepatocytes of various species showed that the compound of formula (I) has good metabolic stability.

Assay Example 4: In Vitro Stability Assay in Liver Microsomes

Purpose of the Assay: Metabolic stabilities of the assay compound in liver microsomes of CD-1 mice, SD rats, beagle dogs, cynomolgus monkeys, and human were assayed, respectively.

Procedure of the Assay: Two 96-well incubation plates were prepared and named T60 incubation plate and NCF60 incubation plate, respectively. 445 μL of microsomal working solutions (liver microsomal protein concentration of 0.56 mg/mL) were added to the T60 incubation plate and the NCF60 incubation plate, respectively, and then the above incubation plates were pre-incubated in a 37° C. water bath for about 10 minutes.

After the pre-incubation, 5 μL of working solutions of the assay sample or the control compound were added to the T60 incubation plate and the NCF60 incubation plate, respectively, and the mixture was mixed well. 50 μL of potassium phosphate buffer was added to each well of the NCF60 incubation plate to initiate the reaction. 180 μL of stop solution (200 ng/mL tolbutamide and 200 ng/mL labetalol in acetonitrile) and 6 uL of NADPH regeneration system working solution were added to the T0 stop plate, and 54 μL of sample was transferred from T60 incubation plate to T0 stop plate (generation of T0 sample). The reaction was initiated by adding 44 μL of NADPH regeneration system working solution to each well of the T60 incubation plate. Only 54 μL of microsome working solution, 6 uL of NADPH regeneration system working solution and 180 μL of stop solution were added to the Blank plate. Therefore, in samples of the assay compound or the control compound, the final reaction concentration of compound, testosterone, diclofenac and propafenone was 1 μM, the concentration of liver microsomes was 0.5 mg/mL, and the final reaction concentrations of DMSO and acetonitrile in the reaction system were 0.01% (v/v) and 0.99% (v/v), respectively. After an appropriate time (e.g., 5, 15, 30, 45 and 60 minutes) of incubation, 180 μL of stop solutions (200 ng/mL tolbutamide and 200 ng/mL labetalol in acetonitrile) were added to the sample wells of each stop plate, respectively. 60 μL of sample was removed from the T60 incubation plate to stop the reaction. All sample plates were shaken well and then centrifuged at 3220×g for 20 minutes. Then 80 μL of supernatant was taken out from each well, and diluted in 240 μL of pure water for liquid chromatography-tandem mass spectrometry analysis. All samples were injected and analyzed by liquid chromatography-tandem mass spectrometry.

Assay Results: The assay results are shown in Table 7.

TABLE 7

Metabolic stability of the assay compound in liver microsomes of CD-1 mice, SD rats, beagle dogs, cynomolgus monkeys, and human

| Assay sample | Species | $T_{1/2}$ (min) | $CL_{int(hep)}$ (μL/min/$10^6$) | $CL_{int(liver)}$ (mL/min/kg) |
|---|---|---|---|---|
| Compound of formula (I) | CD-1 mice | 4.9 | 284.6 | 1126.8 |
| | SD rats | 23.0 | 60.2 | 108.3 |
| | Cynomolgus monkeys | 6.2 | 224.6 | 303.2 |
| | Beagle dogs | >145 | <9.6 | <13.8 |
| | Human | 20.4 | 67.9 | 61.1 |

Conclusion: The assay of the metabolic stability in liver microsomes showed that the compound of formula (I) has good metabolic stability.

Assay Example 5: Stability Assay in Plasma

Purpose of the Assay: Stabilities of the assay compound in plasma of CD-1 mice and human were assayed, respectively.

Procedure of the Assay: Cryopreserved plasma was thawed for 10 to 20 min. After the plasma was completely thawed, it was placed in a centrifuge and centrifuged at 3220×g for 5 min to remove any suspended matter and sediment in the plasma. 96-well incubation plates were prepared and named T0, T10, T30, T60, T120, respectively. 98 μL of blank plasmas of mouse, rat, canine, monkey and human were added to the corresponding incubation plates, then 2 μL of working solutions of the compound or the control compound were added to the corresponding plates in duplicate. All samples were incubated in a 37° C. water bath. The final incubation concentrations of the compound and the control compounds bisacodyl, enalapril maleate, procaine and probanthine were 2 μM, and the final organic phase content was 2.0%. At the end of incubation for each time point, the corresponding incubation plate was removed and 400 μL of a solution of 200 ng/mL of tolbutamide and labetalol in acetonitrile was added to each corresponding sample well to precipitate the protein. All sample plates were sealed and shaken well, and then centrifuged at 3220×g for 20 minutes. 50 μL of supernatant was taken out and diluted in 100 μL of ultrapure water. All samples were mixed well and then analyzed by LC/MS/MS.

Assay Results: The assay results are shown in Table 8.

TABLE 8

Stability of the assay compound in plasma of CD-1 mice and human

| Assay sample | Species | Detection of assay compound content within 120 min |
|---|---|---|
| Compound of formula (I) | CD-1mice | 94% |
| | Human | 93% |

Conclusion: The compound of formula (I) has good stability in plasma of human and mouse.

Assay Example 6: Stability Assay in Whole Blood

Purpose of the Assay: Stabilities of the assay compound in whole blood of CD-1 mice, SD rats, beagle dogs and cynomolgus monkeys were assayed, respectively.

Procedure of the Assay: On the day of the assay or the day before the assay, fresh whole blood from CD-1 mice, SD rats, beagle dogs, and cynomolgus monkeys was collected using anticoagulant EDTA-K2. Prior to the start of the assay, the whole blood was mixed with PBS in 1:1 (v:v) and the mixture was preheated in a 37° C. water bath for 10 to 20 minutes. 96-well incubation plates were prepared and named T0, T30, T60, T240, respectively. In the corresponding incubation plates, including T0, T30, T60 and T240 incubation plates, 2 μL of working solutions of the compound or the control compound were mixed with 98 μL of blank whole blood of mice, rats, canines, monkeys and human in duplicate. All samples were incubated in a 37° C. water bath. The final incubation concentration of the compound was 5 μM and the final incubation concentration of the control compound was 2 μM. At the end of incubation for each time point, the corresponding incubation plate was removed and 100 μL of ultrapure water was immediately added to the corresponding sample wells, and mixed well. 800 μL of a solution of 200 ng/mL tolbutamide and labetalol in acetonitrile was added to precipitate the protein. The sample plates were sealed and shaken well, and then centrifuged at 3220×g for 20 min. 150 μL of supernatant was taken out and analyzed by LC/MS/MS.

Assay Results: The assay results are shown in Table 9.

TABLE 9

Stability of the assay compound in the whole blood of CD-1 mice, SD rats, beagle dogs, and cynomolgus monkeys

| Assay sample | Species | Detection of assay compound content within 240 min |
|---|---|---|
| Compound of formula (I) | CD-1 mice | 117% |
| | SD rats | 115% |
| | Cynomolgus monkeys | 77% |
| | Beagle dogs | 102% |

Conclusion: The stability assay in the whole blood of various species showed that the compound of formula (I) has good stability in whole blood.

Assay Example 7: Assay of Protein Binding Rate

Purpose of the Assay: Protein binding rate of the assay compound in plasma of CD-1 mice, SD rats, beagle dogs, cynomolgus monkeys and human was determined by equilibrium dialysis.

Procedure of the Assay: Plasma samples with a compound concentration of 2 μM were prepared using plasma of the above five species, placed in a 96-well equilibrium dialysis device, and dialyzed with phosphate buffer solution at 37±1° C. for 4 hours. Warfarin was used as the control compound in this assay. The concentrations of the assay compound in plasma and dialysis buffer were determined by LC-MS/MS method.

Assay Results: The assay results are shown in Table 10.

TABLE 10

Protein binding rate of the assay compound in CD-1 mice, SD rats, beagle dogs, cynomolgus monkeys, and human

| Assay sample | Species | Protein unbound rate (%) |
|---|---|---|
| Compound of formula (I) | CD-1 mice | 1.5 |
| | SD rats | 4.8 |
| | Cynomolgus monkeys | 7.8 |
| | Beagle dogs | 3.3 |
| | Human | 4.8 |

Conclusion: Assay on plasma binding rates of various species showed that the compound of formula (I) has high protein unbound rate in plasma.

Assay Example 8: Assay on Pharmacokinetics In Vivo

1) Assay on the Pharmacokinetics of the Assay Compound by Oral Administration and Intravenous Injection in SD Rats The assay compound was mixed with 5% dimethyl sulfoxide/95% (10% hydroxypropyl-β-cyclodextrin) solution. The mixture was vortexed and sonicated to prepare a 1 mg/mL clear solution, which was filtered through a microporous membrane for later use. Male SD rats aged 7 to 10 weeks were selected, and administered candidate compound solutions intravenously or orally. Whole blood was collected for a certain period of time, and prepared to obtain plasma. Drug concentration was analyzed by LC-MS/MS method, and pharmacokinetic parameters were calculated by Phoenix WinNonlin software (Pharsight, USA). The results of the assay are shown in Table 11:

TABLE 11

Pharmacokinetic results of the assay compound

| Route of administration | Pharmacokinetic parameters | Compound of formula (I) |
|---|---|---|
| | Plasma protein unbound rate PPB (Unbound %) | 4.8 |
| Intravenous injection administration | Dose(mg/kg) | 2.0 |
| | Half-life time, $T_{1/2}$ (h) | 1.9 |
| | Clearance rate, CL (ml/min/kg) | 71.5 |
| | Apparent volume of distribution, $Vd_{ss}/Vd_{ss}$, u(L/kg) | 10.6/221 |
| | Area under the plasma concentration-time curve, $AUC_{0-last}/AUC_u$ (nM · h) | 653/31.3 |
| Oral administration | Dose(mg/kg) | 9.8 |
| | Time-to-peak, $T_{max}$ (h) | 1.5 |
| | Peak concentration, $C_{max}/C_{max,\ u}$ (nM) | 220/10.6 |
| | Area under the plasma concentration-time curve, $AUC_{0-last}/AUC_u$ (nM · h) | 995/47.8 |
| | Bioavailability F (%) | 30.5% |

Note:
$Vd_{ss}$, u is the apparent volume of distribution under unbound plasma protein ($Vd_{ss}$, u = $Vd_{ss}$/PPB(Unbound %)); $C_{max,\ u}$, and $AUC_{0-last,\ u}$ are the corresponding values under unbound plasma protein ($C_{max,\ u}$ = $C_{max}$ × PPB(Unbound %); $AUC_{0-last,\ u}$ = $AUC_{0-last}$ × PPB(Unbound %))

Conclusion: PK assay showed that the compound of formula (I) has high unbound plasma exposure and good oral bioavailability in rats.

2) Assay on the Pharmacokinetics of the Crystal Form a of Compound of Formula (II) by Oral Administration in SD Rats 109.72 mg of the assay compound was accurately weighed and added into a glass vial. 774 uL of 0.5% methylcellulose (400 viscosity) aqueous solution was added, and the mixture was stirred for 5 minutes. 10 mL of 0.5% methylcellulose (400 viscosity) aqueous solution was added, and the mixture was stirred for 5 minutes to give a uniform and opaque suspension. Male SD rats aged 7 to 10 weeks were selected, and administered candidate compound solution orally. Whole blood was collected for a certain period of time, and prepared to obtain plasma. Drug concentration was analyzed by LC-MS/MS method, and pharmacokinetic parameters were calculated by Phoenix WinNonlin software (Pharsight, USA). The results of the assay are shown in Table 12:

TABLE 12

Pharmacokinetic results of the assay compound

| Route of administration | Pharmacokinetic parameters | Crystal form A of compound of formula (II) |
|---|---|---|
| Oral administration | Dose(mg/kg) | 92.3 |
| | Time-to-peak, $T_{max}$ (h) | 5.33 |
| | Peak concentration, $C_{max}$ | 1397 |
| | Area under the plasma concentration-time curve, $AUC_{0-last}$ | 11532 |

Conclusion: PK assay showed that crystal form A of compound of formula (II) has high exposure in rats.

3) Assay on the Pharmacokinetics of the Assay Compound by Oral Administration and Intravenous Injection in CD Mice The assay compound was mixed with 5% dimethyl sulfoxide/95% (10% hydroxypropyl-p-cyclodextrin) solution. The mixture was vortexed and sonicated to prepare a 1 mg/mL clear solution, which was filtered through a microporous membrane for later use. Male CD mice aged 7 to 10 weeks were selected, and administered candidate compound solutions intravenously or orally. Whole blood was collected for a certain period of time, and prepared to obtain plasma. Drug concentration was analyzed by LC-MS/MS method, and pharmacokinetic parameters were calculated by Phoenix WinNonlin software (Pharsight, USA). The results of the assay are shown in Table 13:

TABLE 13

Pharmacokinetic results of the assay compound

| Route of administration | Pharmacokinetic parameters | Compound of formula (I) |
|---|---|---|
| | Plasma protein unbound rate PPB (Unbound %) | 12.0 |
| Intravenous injection administration | Dose (mg/kg) | 2.0 |
| | Half-life time, $T_{1/2}$ (h) | 1.7 |
| | Clearance rate, CL (ml/min/kg) | 40.6 |
| | Apparent volume of distribution, $Vd_{ss}/Vd_{ss}$, u(L/kg) | 3.9/32.3 |
| | Area under the plasma concentration-time curve, $AUC_{0-last}/AUC_u$ (nM · h) | 1297/155.6 |

TABLE 13-continued

| Pharmacokinetic results of the assay compound | | |
|---|---|---|
| Route of administration | Pharmacokinetic parameters | Compound of formula (I) |
| Oral administration | Dose(mg/kg) | 10.3 |
| | Time-to-peak, $T_{max}$ (h) | 1.0 |
| | Peak concentration, $C_{max}/C_{max,\ u}$ (nM) | 431/51.7 |
| | Area under the plasma concentration-time curve, $AUC_{0\text{-}last}/AUC_u$ (nM · h) | 1422/170.6 |
| | Bioavailability F (%) | 21.9% |

Note: $Vd_{ss}$,u is the apparent volume of distribution under unbound plasma protein ($Vd_{ss}$,u=$Vd_{ss}$/PPB(Unbound %)); $C_{max,\ u}$, and $AUC_{0\text{-}last,\ u}$, are the corresponding values under unbound plasma protein ($C_{max,u}$=$C_{max}$×PPB(Unbound %); $AUC_{0\text{-}last,\ u}$=$AUC_{0\text{-}last}$×PPB(Unbound %))

Conclusion: PK assay showed that the compound of formula (I) has high unbound plasma exposure and good oral bioavailability in mice.

4) Assay on the Pharmacokinetics of the Assay Compound by Oral Administration in Beagle Dogs 680.397 mg of assay compound powder was accurately weighed, and 50 mL of 0.500 methylcellulose (400 viscosity) aqueous solution was added. The mixture was stirred for 10 minutes, and sonicated for 10 minutes. 50 mL of 0.5% methylcellulose (400 viscosity) aqueous solution was added, and homogenized for 10 minutes using a homogenizer. 11 mL of 0.5% methylcellulose (400 viscosity) aqueous solution was added. The mixture was sonicated for 5 minutes and stirred for 10 minutes. 358 μL of 0.5% methylcellulose (400 viscosity) aqueous solution was added and stirred for 2 minutes. Male beagle dogs aged over six months were selected, and administered candidate compound solution orally. Whole blood was collected for a certain period of time, and prepared to obtain plasma. Drug concentration was analyzed by LC-MS/MS method, and pharmacokinetic parameters were calculated by Phoenix WinNonlin software (Pharsight, USA). The results of the assay are shown in Table 14: Whole blood was collected for a certain period of time, and prepared to obtain plasma. Drug concentration was analyzed by LC-MS/MS method, and pharmacokinetic parameters were calculated by Phoenix WinNonlin software (Pharsight, USA). The results of the assay are shown in Table 14:

TABLE 14

| Pharmacokinetic results of the assay compound | | |
|---|---|---|
| Route of administration | Pharmacokinetic parameters | Crystal form A of compound of formula (II) |
| Oral administration | Dose(mg/kg) | 24.5 |
| | Time-to-peak, $T_{max}$ (h) | 2.50 |
| | Peak concentration, $C_{max}$ | 2435 |
| | Area under the plasma concentration-time curve, $AUC_{0\text{-}last}$ | 16700 |

Conclusion: PK assay showed that the crystal form A of compound of formula (II) has high exposure in dogs.

Assay Example 9: Assay on Pharmacodynamics In Vivo

Assay on pharmacodynamics in vivo in a subcutaneously transplanted tumor model of human pancreatic cancer Mia PaCa-2 cells in Balb/c Nude mice 1. Cell Culture and Tumor Tissue Preparation Cell culture: Human pancreatic cancer Mia PaCa-2 cells (ATCC-CRL-1420) were cultured in monolayer in vitro in DMEM medium with 10% fetal calf serum and 2.5% horse serum in a 37° C., 5% carbon dioxide incubator. Cells were passaged by routine digestion with trypsin-EDTA twice a week. When the cell saturation reached 80%-90% and the cell number met the requirement, the cells were harvested, counted, and resuspended in an appropriate amount of PBS. Matrigel was added in a ratio of 1:1 to obtain a cell suspension with a cell density of $25\times10^6$ cells/mL.

Cell inoculation: 0.2 mL ($5\times10^6$ cells/mouse) of Mia PaCa-2 cells (plus Matrigel, 1:1 by volume) were subcutaneously inoculated into the right back of each mouse. When the average tumor volume reached 190 $mm^3$, mice were randomized into groups based on tumor volume and administration was initiated according to the protocol in Table 15.

TABLE 15

| Assay animal grouping and administration protocol | | | | | | |
|---|---|---|---|---|---|---|
| Group | Number of animals | Compound | Dosage (mg/kg) | Administration volume (μL/g) | Route of administration | Administration frequency |
| 1 | 6 | Vehicle | — | 10 | PO | QD × 22 |
| 2 | 6 | Compound of formula (I) | 10 | 10 | PO | QD × 22 |
| 3 | 6 | Compound of formula (I) | 30 | 10 | PO | QD × 22 |

Note:

PO indicates oral administration; QD indicates once daily.

2. Tumor Measurements and Assay Indicators

Tumor diameter was measured with vernier caliper twice a week. The calculation formula of tumor volume was: $V=0.5a\times b^2$, where a and b represent the long and short diameters of the tumor, respectively.

The anti-tumor efficacy of compound was evaluated by TGI (%) or relative tumor proliferation rate T/C (%). Relative tumor proliferation rate T/C (%)=TRTV/CRTV×100% (TRTV: RTV in a treatment group; CRTV: RTV in a negative control group). The relative tumor volume (RTV) was calculated according to results of tumor measurement, and the calculation formula was RTV=Vt/V0, where V0 was average tumor volume measured at the time of administration by group (i.e., D0), and Vt was average tumor volume at the time of a certain measurement. For TRTV and CRTV, data on the same day were used.

TGI (%) reflected tumor growth inhibition rate. TGI(%)=[(1−(average tumor volume at the end of administration of a treatment group−average tumor volume at the beginning of administration of the treatment group))/(average tumor volume at the end of treatment of a vehicle control group−average tumor volume at the beginning of treatment of the vehicle control group)]×100%.

3. Results of the Assay

Figure 4:
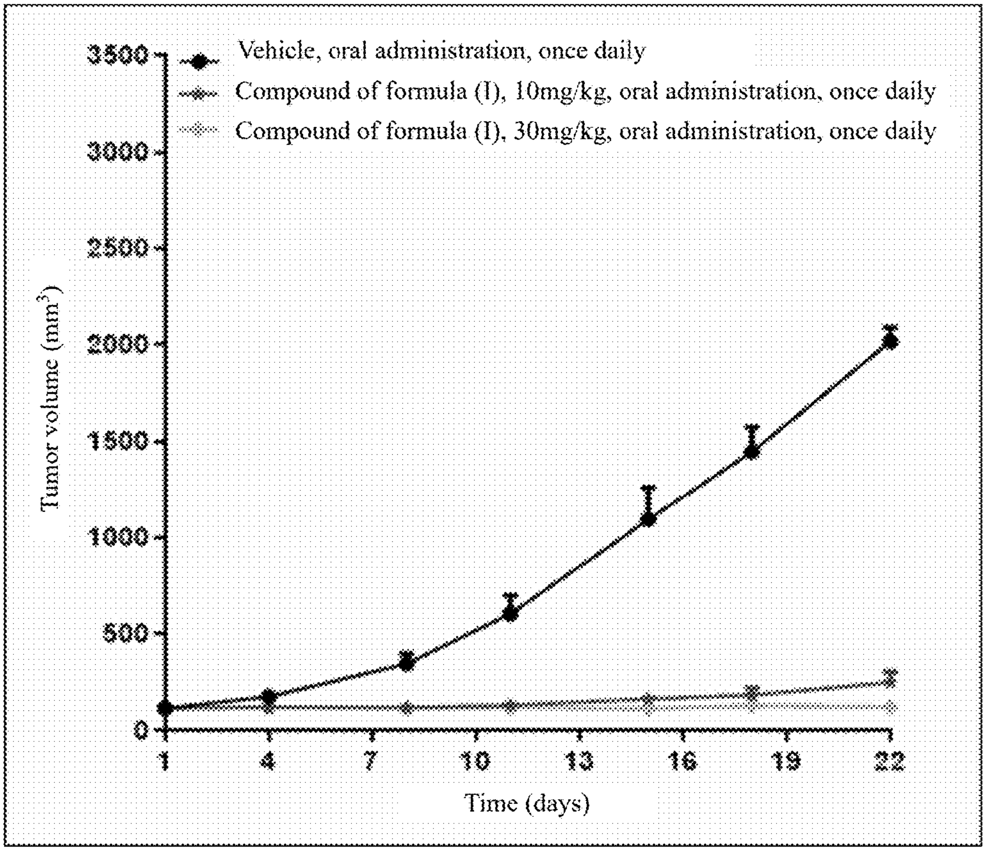
FIG. 4 shows changes in tumor volume over time at different dosages of the compound of formula (I)
Figure 5:
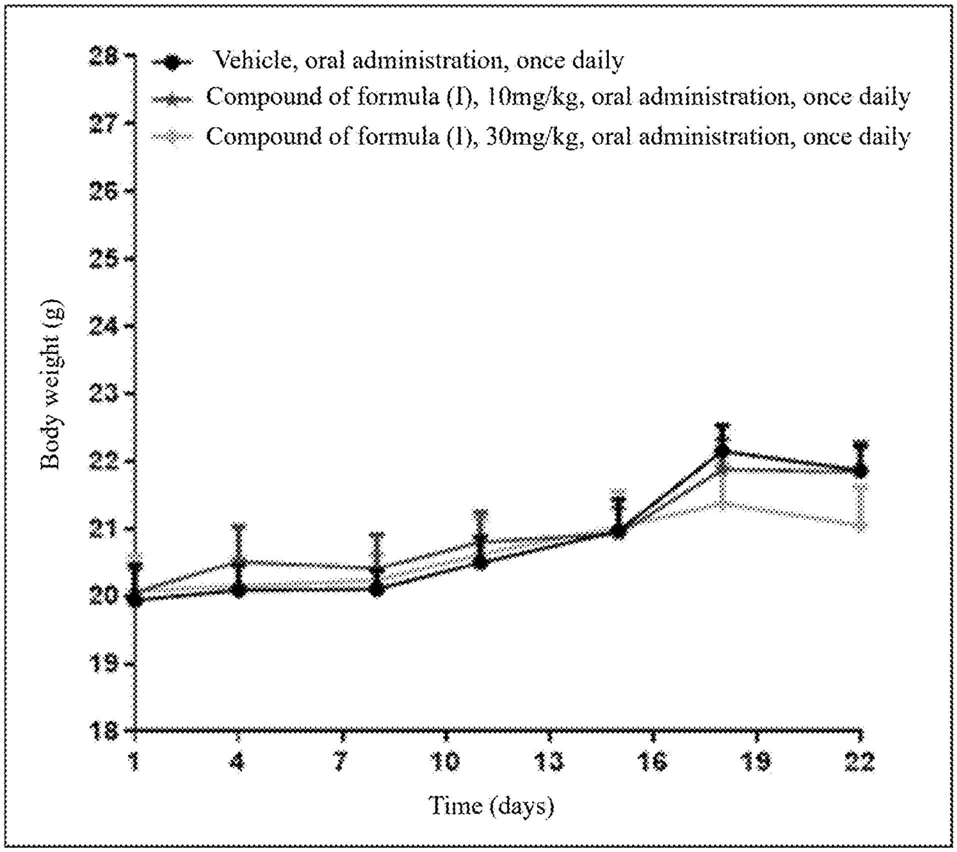
FIG. 5 shows changes in animal body weight over time at different dosages of the compound of formula (I)

The assay results are shown in FIGS. 4 and 5.

The results on day 22 of administration are shown in Table 16.

TABLE 16

T/C and TGI on day 22 of administration

| Compound | Dosage | Average tumor volume | T/C | TGI |
|---|---|---|---|---|
| Vehicle | N/A | 2016.29 $mm^3$ | N/A | N/A |
| Compound of formula (I) | 10 mg/kg | 249.87 $mm^3$ | 12.39% | 93.06% |
| Compound of formula (I) | 30 mg/kg | 124.14 $mm^3$ | 6.16% | 99.64% |

Conclusion: The compound of formula (I) has significant tumor-inhibiting effect. Moreover, the body weight of mice in each dose group is stable, and there is no obvious intolerance.

The invention claimed is:

1. A compound of formula (II), (II)

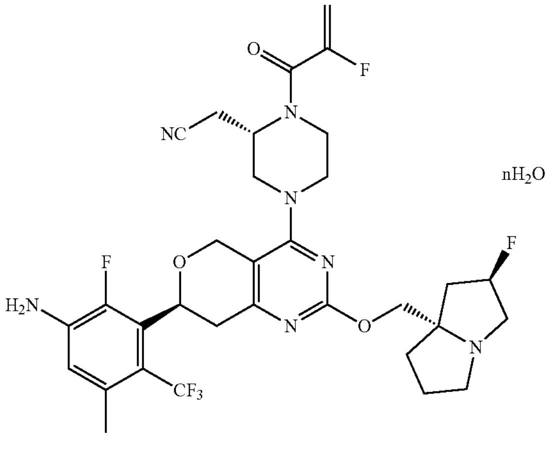

wherein n is 2.

2. A crystal form A of the compound of formula (II) according to claim 1, characterized by an X-ray powder diffraction pattern with characteristic diffraction peaks at 2θ angles of 8.514±0.200°, 14.689±0.200°, and 18.122±0.200°.

3. The crystal form A according to claim 2, which is characterized by X-ray powder diffraction pattern with characteristic diffraction peaks at 2θ angles of 6.218±0.200°, 8.514±0.200°, 12.299±0.200°, 14.689±0.200°, 16.903±0.200°, 18.122±0.200°, 18.927±0.200°, and 25.5800.200°.

4. The crystal form A according to claim 3, which is characterized by X-ray powder diffraction pattern with characteristic diffraction peaks at 2θ angles of 6.218±0.200°, 8.514±0.200°, 11.663±0.200°, 12.299±0.200°, 14.689±0.200°, 16.903±0.200°, 18.122±0.200°, 18.927±0.200°, 19.364±0.200°, 20.386±0.200°, 21.914±0.200°, and 25.580-0.200°.

5. The crystal form A according to claim 4, which is characterized by X-ray powder diffraction pattern with characteristic diffraction peaks at 2θ angles of 6.218°, 8.514°, 11.663°, 12.299°, 14.689°, 16.903°, 18.122°, 18.554°, 18.927°, 19.364°, 20.386°, 21.914°, 22.640°, 23.867°, 24.553°, 24.806°, 25.580°, 25.988°, 27.147°, 27.715°, 29.135°, and 31.799°.

6. The crystal form A according to claim 5, which has an XRPD pattern as shown in FIG. 1.

7. The crystal form A according to claim 2, which has a differential scanning calorimetry (DSC) curve with an endothermic peak at 115.37° C.±3° C.

Figure 2:
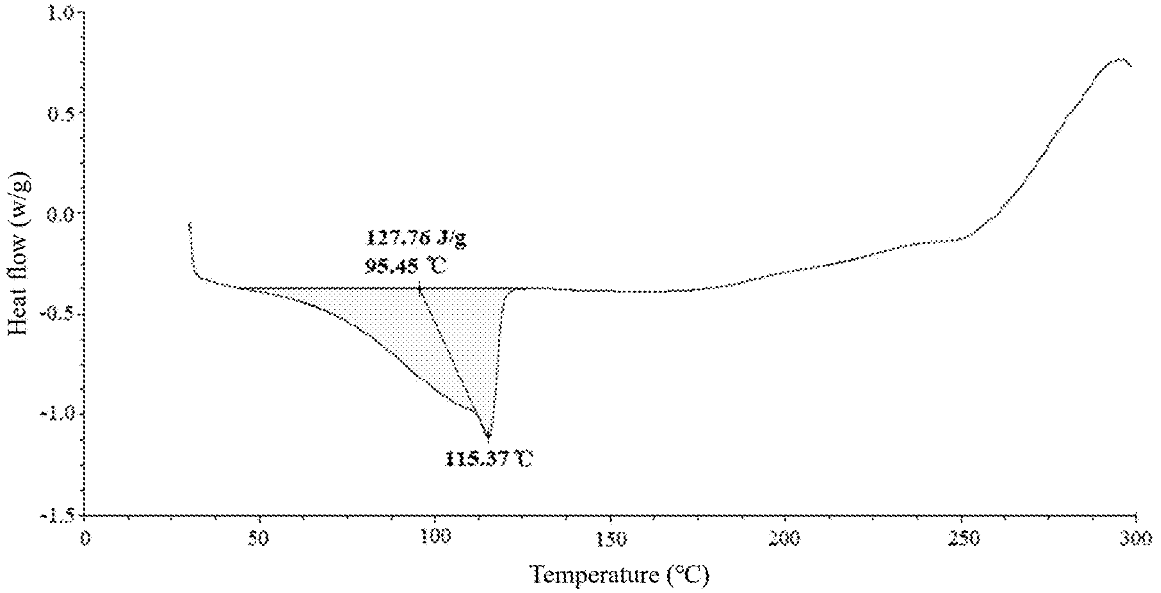
FIG. 2 is the DSC curve of the crystal form A of the compound of formula (II)

8. The crystal form A according to claim 7, which has a DSC curve as shown in FIG. 2.

9. The crystal form A according to claim 2, which has a thermogravimetric analysis (TGA) curve with a weight loss of up to 5.379% at 150.0° C.±3° C.

Figure 3:
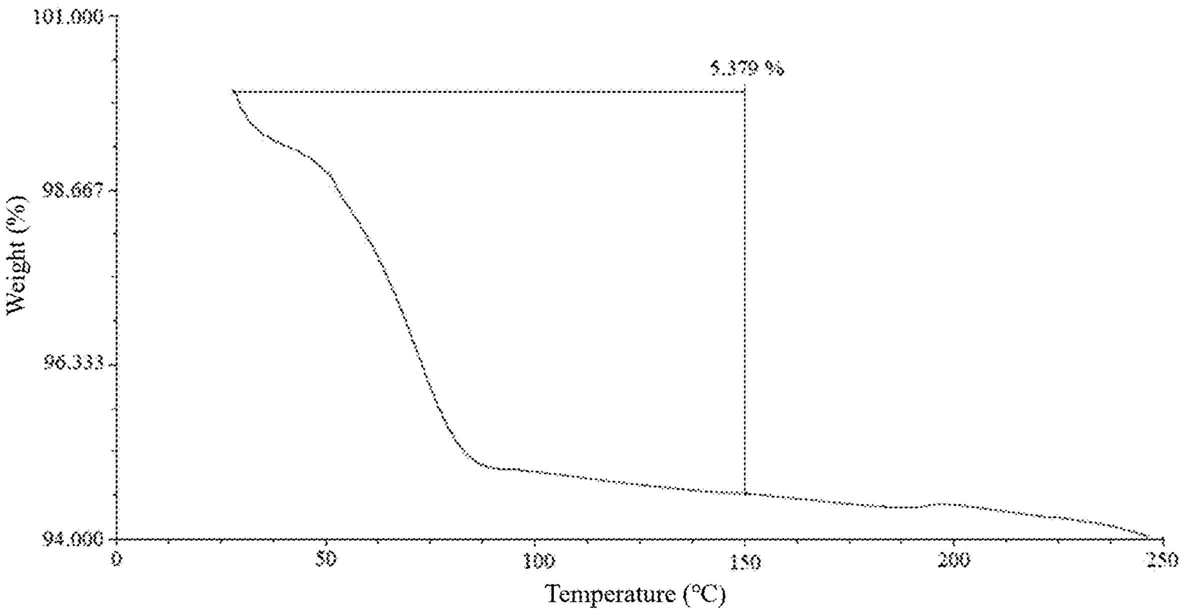
FIG. 3 is the TGA curve of the crystal form A of the compound of formula (II)

10. The crystal form A according to claim 9, which has a TGA curve as shown in FIG. 3.

11. A method of treating lung cancer, pancreatic cancer, or colorectal cancer comprising administering the compound according to claim 1.

12. A method of treating lung cancer, pancreatic cancer, or colorectal cancer comprising administering the crystal form A according to claim 2.

* * * * *